(12) United States Patent
Connon et al.

(10) Patent No.: US 9,050,586 B2
(45) Date of Patent: Jun. 9, 2015

(54) ENANTIOSELECTIVE ORGANIC ANHYDRIDE REACTIONS

(71) Applicants: Stephen J. Connon, Dublin (IE); Sean Tallon, Dublin (IE); Claudio Cornaggia, Dublin (IE); Francesco Manoni, Dublin (IE); Esther Torrente, Dublin (IE)

(72) Inventors: Stephen J. Connon, Dublin (IE); Sean Tallon, Dublin (IE); Claudio Cornaggia, Dublin (IE); Francesco Manoni, Dublin (IE); Esther Torrente, Dublin (IE)

(73) Assignee: THE PROVOST, FELLOWS, FOUNDATION SCHOLARS, AND THE OTHER MEMBERS OF BOARD, OF THE COLLEGE OF THE HOLY AND UNDIVIDED TRINITY OF QUEEN ELIZABETH NEAR DUBLIN, Dublin (IE)

( * ) Notice: Subject to any disclaimer, the term of this patent is extended or adjusted under 35 U.S.C. 154(b) by 0 days.

(21) Appl. No.: 13/800,490

(22) Filed: Mar. 13, 2013

(65) Prior Publication Data

US 2013/0245268 A1    Sep. 19, 2013

(30) Foreign Application Priority Data

Mar. 13, 2012 (EP) .................................... 12159320

(51) Int. Cl.

| | | |
|---|---|---|
| C07D 409/04 | (2006.01) | |
| C07D 311/20 | (2006.01) | |
| C07D 307/33 | (2006.01) | |
| C07D 311/76 | (2006.01) | |
| C07D 453/04 | (2006.01) | |
| C07B 53/00 | (2006.01) | |
| B01J 31/02 | (2006.01) | |

(52) U.S. Cl.
CPC ........... *B01J 31/0271* (2013.01); *C07D 311/76* (2013.01); *C07B 53/00* (2013.01); *C07D 453/04* (2013.01); *C07D 307/33* (2013.01); *C07D 311/20* (2013.01); *C07D 409/04* (2013.01)

(58) Field of Classification Search
USPC ........................................................ 514/456
See application file for complete search history.

(56) References Cited

U.S. PATENT DOCUMENTS

2012/0046468 A1*  2/2012  Connon et al. ................ 546/134

FOREIGN PATENT DOCUMENTS

EP          2 301 931 A1     3/2011

OTHER PUBLICATIONS

Peschiulli; J. Org. Chem. 2008, 73, 6409-6412.*
Dorwold, "Side Reactions in Organic Synthesis" Wiley, 2005, chapter 1.*
Gaunt, Drug Discovery Today, 2007, 12, 8-27.*
Vara, Organic Letters, 2008, 10, 4759-4762.*
Hassan, Synthetic Communications, 2011, 41, 523-527.*
Belokon, Chemical Communications, 2002, 244-245.*
Bassas, Oriol et al., "A Simple Organocatalytic Enantioselective Synthesis of Pregabalin", European Journal of Organic Chemistry (2009), pp. 1340-1351.
Shi, Jian et al., "Asymmetric synthesis of multi-substituted spiro[5,5]undecane-1,5,9-triones via organocatalytic three-component reaction", Tetrahedron (2011), vol. 67, pp. 1781-1787.

* cited by examiner

*Primary Examiner* — John Mabry
*Assistant Examiner* — Daniel Carcanague
(74) *Attorney, Agent, or Firm* — Scully, Scott, Murphy & Presser, P.C.

(57) ABSTRACT

Disclosed herein is enantioselective synthetic method comprising reacting an enolisable $C_4$-$C_{50}$ organic anhydride with a second compound selected from the group consisting of an aldehyde, a ketone, an aldimine, a ketimine or a Michael Acceptor in the presence of a bifunctional organocatalyst. The reaction may find particular utility in the enantioselective synthesis of medicinally relevant heterocycles, such as dihydroisocoumarins and dihydroisoquinolinones.

8 Claims, No Drawings

ENANTIOSELECTIVE ORGANIC ANHYDRIDE REACTIONS

FIELD OF THE INVENTION

The present invention relates to asymmetric synthesis, and in particular the field of asymmetric catalysis. Disclosed herein are a number of novel catalysts for promoting highly useful synthetic transformations between organic anhydrides and aldehydes, ketones, and α,β-unsaturated electrophiles. The transformations of the present invention allow access to densely functionalised products in high enantiomeric excess.

BACKGROUND TO THE INVENTION

Privileged structures are molecular frameworks exhibited in natural products and medicinal compounds that show therapeutic activity at number of different receptor or enzyme targets. Accordingly, facile enantioselective synthetic routes to such structures are valuable and are in constant demand.

Two such privileged structures are Dihydroisocoumarins (A) and Dihydroisoquinolinones (B). The asterisks denote carbon atoms that are chiral. Given the effect the chirality of these stereogenic carbons may have on the activity of these molecules, controlling the absolute stereochemistry of the substituents on these carbon atoms is.

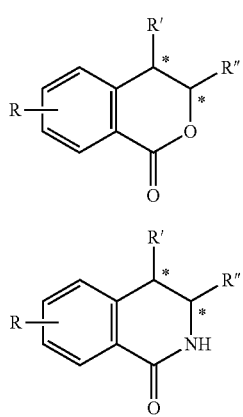

Molecules possessing the bicyclic dihydroisocoumarin structural unit exhibit broad spectrum activity and have been reported as cytotoxic/antiproliferative agents, phytotoxic agents, antimicrobial agents, antifungal agents, antiulcer agents, antimalarial agents, anti-inflammatory agents, antioxidant agents and antiallergic properties.

For example, European Patent Application No. 2 301 931 discloses a class of chiral dihydroisocoumarins functionalised with imidazoles (C):

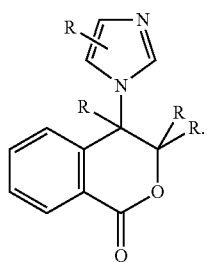

The compounds are indicated as being clinically useful in the treatment of diseases mediated by abnormal activity of aldosterone synthase, such as coronary heart disease or renal failure.

European Patent Application No. 2 301 931 discloses two separate routes to the compounds of interest, neither of which readily lends itself to an enantioselective variant. In particular, EP2 301 931 discloses the resolution of the racemic compounds by means of methods known in the art, such as diastereomeric crystallisation and chiral HPLC. Naturally, discarding the unwanted enantiomer is wasteful and a more elegant enantioselective synthesis would be preferable.

Accordingly, there remains a need for alternative synthetic routes to these, and other privileged heterocyclic structures in which the chirality of any stereogenic carbons can be readily controlled.

Bassas et al. (Eur. J. Org. Chem. 2009, 1340) employed a bifunctional organocatalyst, to catalyse the conjugate addition of Meldrum's acid (a cyclic ester) to a nitroalkene, in a synthesis of Pregabalin.

Shi et al. (Tetrahedron, 2011, 67, 1781) employed a bifunctional organocatalyst, to catalyse a three-component Knoevanagel-Diels-Alder addition reaction involving enones aldehydes and Meldrum's acid (a cyclic ester).

SUMMARY OF THE INVENTION

The present invention provides an inventive enantioselective method for the preparation of highly functionalised heterocycles, such as benzofused heterocycles. Complementary to the inventive methodology, the present invention also provides for a novel class of metal free, small, organic molecule catalysts that are highly effective in the enantioselective synthetic methodology of the present invention.

In a first aspect, the present invention provides for an enantioselective synthetic method comprising the step of:
reacting an enolisable $C_4$-$C_{50}$ organic anhydride with a second compound selected from the group consisting of an aldehyde, a ketone, an aldimine, a ketimine or a Michael Acceptor in the presence of a bifunctional organocatalyst.

As used herein the term enantioselective is utilised to refer to a synthetic methodology that produces one enantiomer of a chiral molecule in preference to the other enantiomer. For example, the synthetic methodology of the present invention may produce one enantiomer of the chiral molecule in an enantiomeric excess of at least 50%. Suitably, the synthetic methodology of the present invention may produce one enantiomer of the chiral molecule in an enantiomeric excess of at least 75%. Preferably, the synthetic methodology of the present invention may produce one enantiomer of the chiral molecule in an enantiomeric excess of at least 90%.

In embodiments where the chiral molecule produced by the synthetic methodology of the present invention has at least two chiral centres, the synthetic methodology of the present invention may also be diastereoselective. As used herein the term diastereoselective is utilised to refer to a synthetic methodology that produces one diastereomer of a chiral molecule in preference to the other diastereomer. For example, the synthetic methodology of the present invention may produce one diastereomer of the chiral molecule in a diastereomeric excess of at least 40%. Suitably, the synthetic methodology of the present invention may produce one diastereomer of the chiral molecule in a diastereomeric excess of at least 60%. Preferably, the synthetic methodology of the present invention may produce one diastereomer of the chiral molecule in a diastereomeric excess of at least 90%.

Within this specification the terms enantiomeric excess and diastereomeric excess take their accepted meanings, i.e. {[(major stereoisomer−minor stereoisomer)/(major stereoisomer+minor stereoisomer)]×100}.

The method of the present invention may be carried out at ambient temperature, or below. For example, method of the present invention may be carried out at 20° C., 0° C., −15° C., or −30° C.

The method of the present invention may be carried out in a solvent selected from the group consisting of $C_5$-$C_{12}$ hydrocarbons, $C_6$-$C_{12}$ aromatic hydrocarbons, $C_3$-$C_{12}$ ketones (cyclic and acyclic), $C_2$-$C_{12}$ ethers (cyclic and acyclic), $C_2$ to $C_{12}$ esters (cyclic and acyclic), $C_2$-$C_5$ nitriles and combinations thereof. Desirably, the solvent is ethereal. For example, $C_2$-$C_{12}$ ethers (cyclic and acyclic). Suitable ethers may be selected from the group consisting of diethylether, THF, 2-methyl THF, diisopropylether, methyltertbutylether (MTBE) and combinations thereof. In a preferred embodiment, the solvent is methyltertbutylether (MTBE). The present inventors have found that the use of ethereal solvents results in optimal performance when anhydride reaction components are utilised in the presence of bifunctional organocatalysts.

With reference to the method of the present invention, the second compound selected from the group consisting of an aldehyde, a ketone, an aldimine, a ketimine or a Michael Acceptor may be of the general formula (A):

(A)

wherein, $R^1$ and $R^2$ are the same or different and are independently selected from the group consisting of H, $C_1$-$C_{20}$ aliphatic, $C_1$-$C_{20}$ heteroaliphatic, $C_3$-$C_{20}$ cycloaliphatic, $C_2$-$C_{20}$ heterocycloaliphatic, $C_5$-$C_{20}$ aryl, $C_3$-$C_{20}$ heteroaryl, and combinations thereof; or $R^1$ and $R^2$ together with the carbon to which they are attached define a $C_3$-$C_{20}$ cycloaliphatic ring, or a $C_2$-$C_{20}$ heterocycloaliphatic ring;

the moiety C—Z is selected from the group consisting of C=O, C=NR$^3$, and C=CR$^5$R$^4$;

$R^3$ is selected from the group consisting of $C_1$-$C_{10}$ aliphatic, $C_3$-$C_{10}$ cycloaliphatic, benzyl, benzhydryl, trityl, C(=O)OR$^6$, C(=O)NH$_2$, C(=O)NHR$^6$, C(=O)NR$^6$R$^7$, —OH, OR$^6$, OC(=O)R$^6$, OC(=O)OR$^6$, OC(=O)NH$_2$, OC(=O)NHR$^6$, OC(=O)NR$^6$R$^7$, NH$_2$, NHR$^6$, NR$^6$R$^7$, N(H)C(=O)R$^6$, N(R$^6$)C(=O)R$^7$, N(H)C(=O)OR$^6$, N(R$^6$)C(=O)OR$^7$, N(H)C(=O)NH$_2$, N(R$^6$)C(=O)NH$_2$, N(H)C(=O)NHR$^6$, N(R$^6$)C(=O)NHR$^7$, N(H)C(=O)NR$^6$R$^7$, N(R$^6$)C(=O)NR$^7$R$^8$, S(=O)R$^6$, S(=O)$_2$R$^6$, P(=O)R$^6$R$^7$, P(=O)(OH)(OH), P(=O)(OH)(OR$^6$), P(=O)(OR$^6$)(OR$^7$); or $R^3$ together with $R^1$, and C=N define a $C_3$-$C_{20}$ heterocycloaliphatic ring;

$R^4$ is selected from the group consisting of C(=O)H, C(=O)R$^6$, C(=O)OH, C(=O)OR$^6$, C(=O)NH$_2$, C(=O)NHR$^6$, C(=O)NR$^6$R$^7$, S(=O)R$^6$, S(=O)$_2$R$^6$, P(=O)R$^6$R$^7$, P(=O)(OH)(OH), P(=O)(OH)(OR$^6$), P(=O)(OR$^6$)(OR$^7$), C=N, and NO$_2$;

$R^5$ is selected from the group consisting of H, F, Cl, Br, I, C=N, $C_1$-$C_{20}$ aliphatic, $C_1$-$C_{20}$ heteroaliphatic, $C_3$-$C_{20}$ cycloaliphatic, $C_2$-$C_{20}$ heterocycloaliphatic, $C_5$-$C_{20}$ aryl, $C_3$-$C_{20}$ heteroaryl, C(=O)H, C(=O)R$^6$, C(=O)OH, C(=O)OR$^6$, C(=O)NH$_2$, C(=O)NHR$^6$, C(=O)NR$^6$R$^7$, S(=O)R$^6$, S(=O)$_2$R$^6$, P(=O)R$^6$R$^7$, P(=O)(OH)(OH), P(=O)(OH)(OR$^6$), P(=O)(OR$^6$)(OR$^7$), and NO$_2$; and $R^6$, $R^7$ and $R^8$ are the same or different and are independently selected from the group consisting of $C_1$-$C_{20}$ aliphatic, $C_1$-$C_{20}$ heteroaliphatic, $C_3$-$C_{20}$ cycloaliphatic, $C_2$-$C_{20}$ heterocycloaliphatic, $C_5$-$C_{20}$ aryl, $C_3$-$C_{20}$ heteroaryl, and combinations thereof.

With reference to the method of the present invention, the second compound may be an aldehyde or ketone of the formula:

wherein:

$R^1$ and $R^2$ are the same or different and are independently selected from the group consisting of H, $C_1$-$C_{20}$ aliphatic, $C_1$-$C_{20}$ heteroaliphatic, $C_3$-$C_{20}$ cycloaliphatic, $C_2$-$C_{20}$ heterocycloaliphatic, $C_5$-$C_{20}$ aryl, $C_3$-$C_{20}$ heteroaryl, and combinations thereof; or $R^1$ and $R^2$ together with the carbon to which they are attached define a $C_3$-$C_{20}$ cycloaliphatic ring, or a $C_2$-$C_{20}$ heterocycloaliphatic ring.

In one embodiment, the second compound may be an aldehyde of the formula:

wherein:

$R^1$ is selected from the group consisting of $C_1$-$C_{20}$ aliphatic, $C_1$-$C_{20}$ heteroaliphatic, $C_3$-$C_{20}$ cycloaliphatic, $C_2$-$C_{20}$ heterocycloaliphatic, $C_5$-$C_{20}$ aryl, $C_3$-$C_{20}$ heteroaryl, and combinations thereof.

As will be appreciated by a person skilled in the art, unless otherwise specified, the definitions of $C_x$-$C_y$ aliphatic, $C_x$-$C_y$ cycloaliphatic, $C_x$-$C_y$ heteroaliphatic, $C_x$-$C_y$ heterocycloaliphatic, $C_x$-$C_y$ aromatic/aryl, $C_x$-$C_y$ heteroaryl, etc. include substitution of these chains/rings with substituents such as halogens, CF$_3$, CCl$_3$, CBr$_3$, NO$_2$, CN, provided such substitutions do not interfere with the efficient catalysis of the synthetic method of the present invention.

As used herein the term enolisable refers to an organic anhydride that is capable of undergoing keto/enol tautomerism. For example, in the scheme below glutaric anhydride is an enolisable anhydride—it has protons alpha to the carbonyl groups and it can form an enol tautomer. Conversely, phthalic anhydride has no alpha protons and it is not considered to be an enolisable organic anhydride.

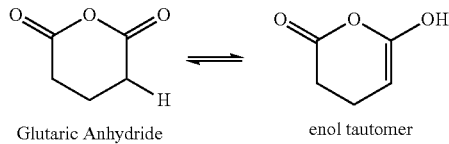

Glutaric Anhydride          enol tautomer

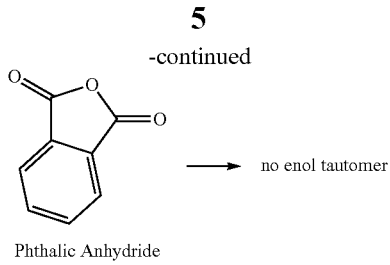

Phthalic Anhydride → no enol tautomer

With reference to the method of the present invention, the enolisable $C_4$-$C_{50}$ organic anhydride may be a cyclic anhydride. The enolisable $C_4$-$C_{50}$ cyclic organic anhydride may be selected from the group consisting of:

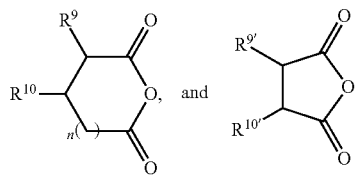

wherein, $R^9$, $R^{9'}$, $R^{10}$ and $R^{10'}$ are the same or different and are independently selected from the group consisting of H, halogen, C≡N, $NO_2$, $C_1$-$C_5$ haloalkyl, $C_1$-$C_{20}$ aliphatic, $C_1$-$C_{20}$ heteroaliphatic, $C_3$-$C_{20}$ cycloaliphatic, $C_2$-$C_{20}$ heterocycloaliphatic, $C_5$-$C_{20}$ aryl, $C_3$-$C_{20}$ heteroaryl, C(=O)$OR^6$, C(=O)$NH_2$, C(=O)$NHR^6$, C(=O)$NR^6R^7$, $OR^6$, OC(=O)$R^6$, OC(=O)$OR^6$, OC(=O)$NH_2$, OC(=O)$NHR^6$, OC(=O)$NR^6R^7$, N(H)C(=O)$R^6$, N($R^6$)C(=O)$R^7$, N(H)C(=O)$OR^6$, N($R^6$)C(=O)$OR^7$, N(H)C(=O)$NH_2$, N($R^6$)C(=O)$NH_2$, N(H)C(=O)$NHR^6$, N($R^6$)C(=O)$NHR^7$, N(H)C(=O)$NR^6R^7$, N($R^6$)C(=O)$NR^7R^8$, S(=O)$R^6$, S(=O)$_2R^6$, P(=O)$R^6R^7$, P(=O)(OH)(OH), P(=O)(OH)($OR^6$), P(=O)($OR^6$)($OR^7$); or $R^9$ and $R^{10}$ together with the carbon atoms to which they are attached define a $C_3$-$C_{20}$ cycloaliphatic ring, a $C_2$-$C_{20}$ heterocycloaliphatic ring, a $C_5$-$C_{20}$ aryl ring, or a $C_3$-$C_{20}$ heteroaryl ring; or $R^{9'}$ and $R^{10'}$ together with the carbon atoms to which they are attached define a $C_3$-$C_{20}$ cycloaliphatic ring, or a $C_2$-$C_{20}$ heterocycloaliphatic ring subject to the proviso that at least one of the carbon atoms to which $R^{9'}$ and $R^{10'}$ are attached is saturated;

$R^6$, $R^7$ and $R^8$ are the same or different and are independently selected from the group consisting of $C_1$-$C_{20}$ aliphatic, $C_1$-$C_{20}$ heteroaliphatic, $C_3$-$C_{20}$ cycloaliphatic, $C_2$-$C_{20}$ heterocycloaliphatic, $C_5$-$C_{20}$ aryl, $C_3$-$C_{20}$ heteroaryl, and combinations thereof; and n is 1-5.

The enolisable $C_4$-$C_{50}$ cyclic organic anhydride may be of the general formula:

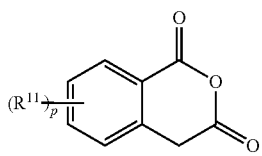

wherein:

p is 0-4;

each occurrence of $R^{11}$ is independently selected from the group consisting of $C_1$-$C_{10}$ aliphatic, $C_3$-$C_{10}$ cycloaliphatic C(=O)$OR^6$, C(=O)$NH_2$, C(=O)$NHR^6$, C(=O)$NR^6R^7$, $OR^6$, OC(=O)$R^6$, OC(=O)$OR^6$, OC(=O)$NH_2$, OC(=O)$NHR^6$, OC(=O)$NR^6R^7$, N(H)C(=O)$R^6$, N($R^6$)C(=O)$R^7$, N(H)C(=O)$OR^6$, N($R^6$)C(=O)$OR^7$, N(H)C(=O)$NH_2$, N($R^6$)C(=O)$NH_2$, N(H)C(=O)$NHR^6$, N($R^6$)C(=O)$NHR^7$, N(H)C(=O)$NR^6R^7$, N($R^6$)C(=O)$NR^7R^8$, S(=O)$R^6$, S(=O)$_2R^6$, P(=O)$R^6R^7$, P(=O)(OH)(OH), P(=O)(OH)($OR^6$), P(=O)($OR^6$)($OR^7$), C≡N, $NO_2$, $CH_2F$, $CHF_2$, $CF_3$, Cl, Br, F, I and combinations thereof; or where p≥2 each $R^{11}$ and the carbon atoms to which they are attached may define a $C_5$-$C_{20}$ cycloaliphatic ring, a $C_2$-$C_{20}$ heterocycloaliphatic ring, a $C_5$-$C_{20}$ aryl ring, or a $C_3$-$C_{20}$ heteroaryl ring; and $R^6$, $R^7$ and $R^8$ are the same or different and are independently selected from the group consisting of $C_1$-$C_{20}$ aliphatic, $C_1$-$C_{20}$ heteroaliphatic, $C_3$-$C_{20}$ cycloaliphatic, $C_2$-$C_{20}$ heterocycloaliphatic, $C_5$-$C_{20}$ aryl, $C_3$-$C_{20}$ heteroaryl, and combinations thereof.

The enolisable $C_4$-$C_{50}$ cyclic organic anhydride may be:

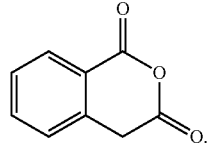 [SMILES: O=C1Cc2ccccc2C(=O)O1]

Within this specification, the term bifunctional organocatalyst refers to a chiral, small organic molecule (i.e., non-metal based) having a Lewis acid moiety and a Lewis base moiety within the molecule, and between 5 and 60 carbon atoms. The bifunctional organocatalyst is used in sub-stoichiometric loading relative to at least one of the reactants. The bifunctional organocatalyst may be used in substoichiometric loading relative to the organic anhydride component.

As used herein the terms Lewis acid moiety and a Lewis base moiety take their accepted meanings, i.e. a Lewis acid moiety is a moiety which accepts an electron pair and a Lewis base moiety is a moiety which donates an electron pair.

Suitably, the bifunctional organocatalyst or chiral small organic molecule is substantially enantiopure. This is important for highly selective asymmetric catalysis of the reaction between the anhydride and the second compound selected from the group consisting of an aldehyde, a ketone, an aldimine, a ketimine or a Michael Acceptor. The bifunctional organocatalyst may function by enhancing the nucleophilicity of a first reaction component and enhancing the electrophilicity of a second reaction component. For example, the bifunctional organocatalyst may enhance the electrophilicity of an aldehyde or Michael Acceptor and generate a nucleophile by promoting the formation of an enol within the organic anhydride, thereby facilitating reaction of both components in a chiral environment. A schematic of a bifunctional organocatalyst is detailed below:

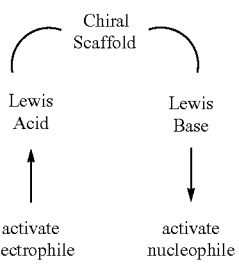

The catalyst loading with respect to the organic anhydride may be 0.1-50 mol %, for example 0.1-25 mol %, such as 0.1-10 mol %. Desirably, the catalyst loading with respect to the organic anhydride is 5-10 mol %. Advantageously, this represents a highly economic and efficient catalyst loading.

The bifunctional organocatalyst may be selected from the group consisting of:

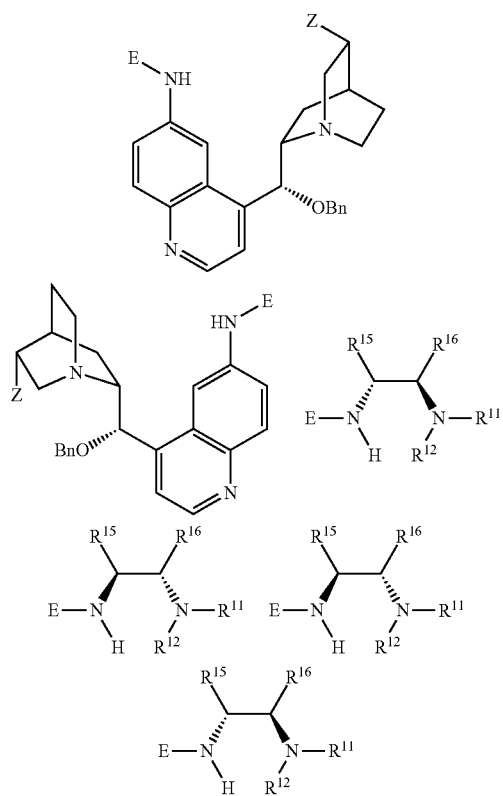

wherein
E is a moiety selected from the group consisting of:

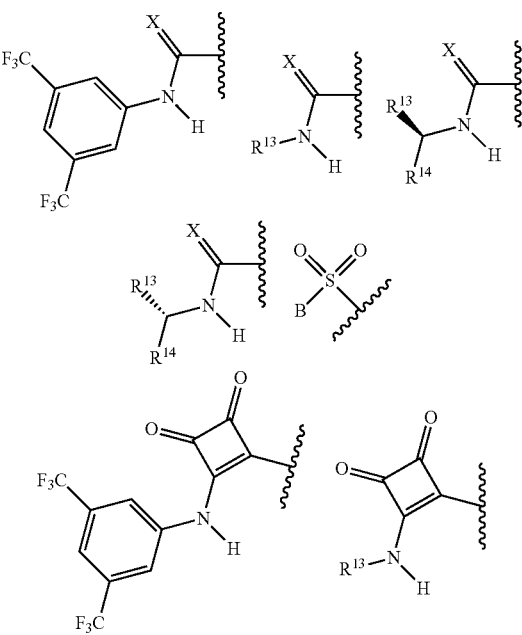

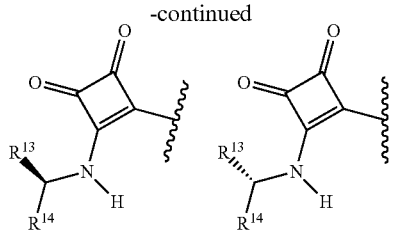

X is O or S;

B is selected from the group consisting of $C_1$-$C_{20}$ aliphatic, $C_1$-$C_{20}$ heteroaliphatic, $C_3$-$C_{20}$ cycloaliphatic, $C_2$-$C_{20}$ heterocycloaliphatic, $C_5$-$C_{20}$ aryl, $C_3$-$C_{20}$ heteroaryl, and combinations thereof optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof;

$R^{11}$ and $R^{12}$ are the same or different and are independently selected from the group consisting of $C_1$-$C_{20}$ aliphatic, and $C_3$-$C_{20}$ cycloaliphatic optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof; or $R^{11}$ and $R^{12}$ together with the nitrogen atom to which they are attached define a $C_3$-$C_{20}$ heterocycloaliphatic ring optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof;

$R^{13}$ and $R^{14}$ are the same or different and are independently selected from the group consisting of $C_1$-$C_{20}$ aliphatic, $C_1$-$C_{20}$ heteroaliphatic, $C_3$-$C_{20}$ cycloaliphatic, $C_2$-$C_{20}$ heterocycloaliphatic, $C_5$-$C_{20}$ aryl, $C_3$-$C_{20}$ heteroaryl, and combinations thereof optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof; or $R^{13}$ and $R^{14}$ together with the carbon atom to which they are attached define a $C_3$-$C_{20}$ cycloaliphatic ring, $C_2$-$C_{20}$ heterocycloaliphatic ring, $C_5$-$C_{20}$ aryl ring, $C_3$-$C_{20}$ heteroaryl ring optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof; and $R^{15}$ and $R^{16}$ are the same or different and are independently selected from the group consisting of $C_1$-$C_{20}$ aliphatic, $C_1$-$C_{20}$ heteroaliphatic, $C_3$-$C_{20}$ cycloaliphatic, $C_2$-$C_{20}$ heterocycloaliphatic, $C_5$-$C_{20}$ aryl, $C_3$-$C_{20}$ heteroaryl, and combinations thereof optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof; or $R^{15}$ and $R^{18}$ together with the carbon atoms to which they are attached define $C_3$-$C_{20}$ cycloaliphatic, $C_2$-$C_{20}$ heterocycloaliphatic, $C_5$-$C_{20}$ aryl, $C_3$-$C_{20}$ heteroaryl optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof.

In a preferred embodiment, the bifunctional organocatalyst comprises a cinchona alkaloid or a synthetic derivative of a cinchona alkaloid.

The bifunctional organocatalyst may be selected from the group consisting of:

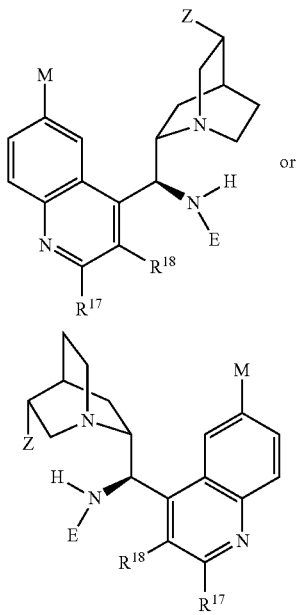

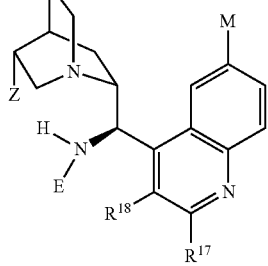

wherein

Z is $C_1$-$C_5$ aliphatic optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide and combinations thereof;

M is selected from the group consisting of H, OH, SH, O($C_1$-$C_5$ aliphatic), and S($C_1$-$C_5$ aliphatic);

$R^{17}$ and $R^{18}$ are the same or different and are independently selected from the group consisting of H, $C_3$-$C_{10}$ branched aliphatic, $C_3$-$C_{10}$ branched heteroaliphatic, $C_3$-$C_{20}$ cycloaliphatic, $C_2$-$C_{20}$ heterocycloaliphatic, $C_5$-$C_{20}$ aryl, $C_3$-$C_{20}$ heteroaryl, Br, I and combinations thereof; or $R^{17}$ and $R^{18}$ together with the carbon atoms to which they are attached define a monocyclic or polycyclic structure selected from the group consisting of $C_3$-$C_{20}$ cycloaliphatic, $C_2$-$C_{20}$ heterocycloaliphatic, $C_5$-$C_{20}$ aryl, $C_3$-$C_{20}$ heteroaryl; and E is a moiety selected from the group consisting of:

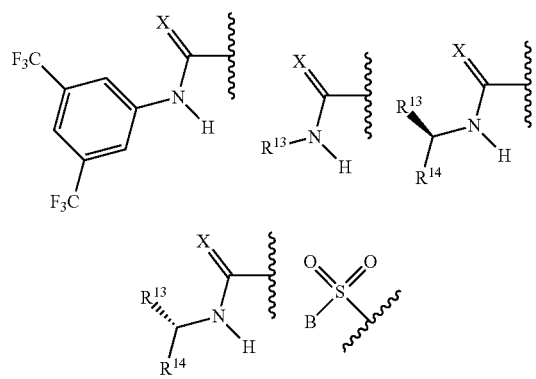

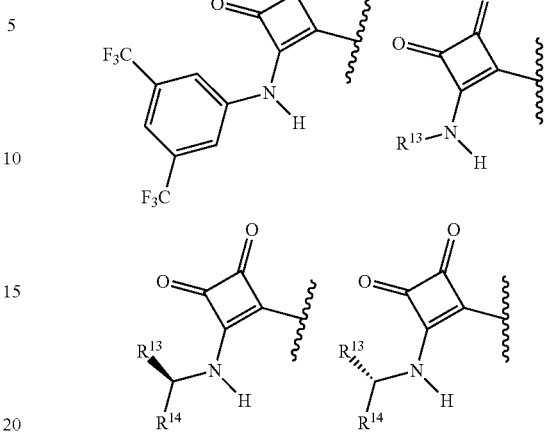

wherein X can be O or S;

B is selected from the group consisting of $C_1$-$C_{20}$ aliphatic, $C_1$-$C_{20}$ heteroaliphatic, $C_3$-$C_{20}$ cycloaliphatic, $C_2$-$C_{20}$ heterocycloaliphatic, $C_5$-$C_{20}$ aryl, $C_3$-$C_{20}$ heteroaryl, and combinations thereof optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof;

$R^{13}$ and $R^{14}$ are the same or different and are independently selected from the group consisting of $C_1$-$C_{20}$ aliphatic, $C_1$-$C_{20}$ heteroaliphatic, $C_3$-$C_{20}$ cycloaliphatic, $C_2$-$C_{20}$ heterocycloaliphatic, $C_5$-$C_{20}$ aryl, $C_3$-$C_{20}$ heteroaryl, and combinations thereof optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof; or $R^{13}$ and $R^{14}$ together with the carbon atom to which they are attached define a $C_3$-$C_{20}$ cycloaliphatic ring, $C_2$-$C_{20}$ heterocycloaliphatic ring, $C_5$-$C_{20}$ aryl ring, $C_3$-$C_{20}$ heteroaryl ring optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof.

The squiggle line on the moiety E indicates bonding to the nitrogen at C9 of the cinchona alkaloid.

The bifunctional organocatalyst may be selected from the group consisting of:

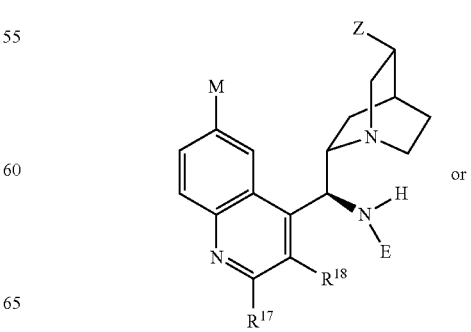

-continued

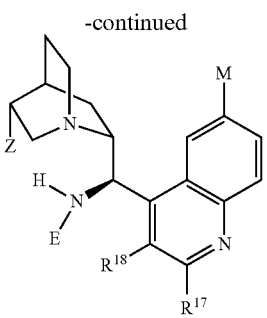

wherein

Z is $C_1$-$C_5$ aliphatic optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide and combinations thereof;

M is selected from the group consisting of H, OH, SH, O($C_1$-$C_5$ aliphatic), and S($C_1$-$C_5$ aliphatic);

$R^{17}$ and $R^{18}$ are the same or different and are independently selected from the group consisting of H, $C_3$-$C_{10}$ branched aliphatic, $C_3$-$C_{10}$ branched heteroaliphatic, $C_3$-$C_{20}$ cycloaliphatic, $C_2$-$C_{20}$ heterocycloaliphatic, $C_5$-$C_{20}$ aryl, $C_3$-$C_{20}$ heteroaryl, Br, I and combinations thereof; or $R^{17}$ and $R^{18}$ together with the carbon atoms to which they are attached define a monocyclic or polycyclic structure selected from the group consisting of $C_3$-$C_{20}$ cycloaliphatic, $C_2$-$C_{20}$ heterocycloaliphatic, $C_5$-$C_{20}$ aryl, $C_3$-$C_{20}$ heteroaryl; and E is a moiety selected from the group consisting of:

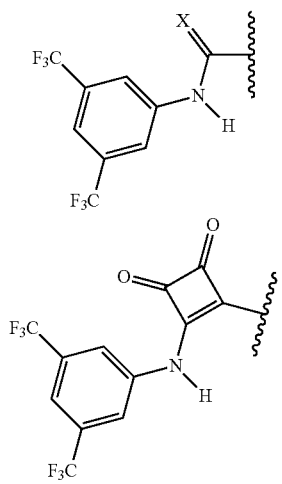

wherein X can be O or S.

Surprisingly, the present inventors have found that in the presence of a sufficiently electrophilic species (e.g., an aldehyde) and a bifunctional organocatalyst, an inherently electrophilic species (i.e., the enolisable organic anhydride) can be persuaded to attack an aldehyde/other electrophile as a nucleophile, without either reacting with itself (an anhydride is usually regarded as a more reactive electrophile than an aldehyde) or the catalyst in a deleterious fashion.

The present inventors have found, somewhat counter intuitively given the propensity of organic anhydrides to act as electrophiles, that a bifunctional organocatalyst could be employed to activate an enolisable anhydride as a nucleophile through catalysis of the equilibrium between it and its enol form. Further surprisingly, the catalyst acts to suppress the anhydride's propensity to act as an electrophile and preferentially activates the second electrophilic component (e.g., an aldehyde) through hydrogen bond donation/general acid catalysis in a controlled chiral environment.

In one embodiment of the synthetic method of the present invention:

1) the $C_4$-$C_{50}$ organic anhydride is selected from the group consisting of:

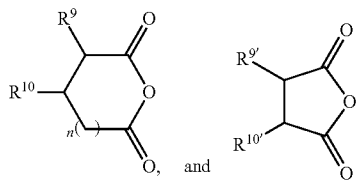

wherein, $R^9$, $R^{9'}$, $R^{10}$ and $R^{10'}$ are the same or different and are independently selected from the group consisting of H, halogen, C≡N, $NO_2$, $C_1$-$C_5$ haloalkyl, $C_1$-$C_{20}$ aliphatic, $C_1$-$C_{20}$ heteroaliphatic, $C_3$-$C_{20}$ cycloaliphatic, $C_2$-$C_{20}$ heterocycloaliphatic, $C_5$-$C_{20}$ aryl, $C_3$-$C_{20}$ heteroaryl, C(=O)$OR^6$, C(=O)$NH_2$, C(=O)$NHR^6$, C(=O)$NR^6R^7$, $OR^6$, OC(=O)$R^6$, OC(=O)$OR^6$, OC(=O)$NH_2$, OC(=O)$NHR^6$, OC(=O)$NR^6R^7$, N(H)C(=O)$R^6$, N($R^6$)C(=O)$R^7$, N(H)C(=O)$OR^6$, N($R^6$)C(=O)$OR^7$, N(H)C(=O)$NH_2$, N($R^6$)C(=O)$NH_2$, N(H)C(=O)$NHR^6$, N($R^6$)C(=O)$NHR^7$, N(H)C(=O)$NR^6R^7$, N($R^6$)C(=O)$NR^7R^8$, S(=O)$R^6$, S(=O)$_2R^6$, P(=O)$R^6R^7$, P(=O)(OH)(OH), P(=O)(OH)($OR^6$), P(=O)($OR^6$)($OR^7$); or $R^9$ and $R^{10}$ together with the carbon atoms to which they are attached define a $C_3$-$C_{20}$ cycloaliphatic ring, a $C_2$-$C_{20}$ heterocycloaliphatic ring, a $C_5$-$C_{20}$ aryl ring, or a $C_3$-$C_{20}$ heteroaryl ring; or $R^{9'}$ and $R^{10'}$ together with the carbon atoms to which they are attached define a $C_3$-$C_{20}$ cycloaliphatic ring, or a $C_2$-$C_{20}$ heterocycloaliphatic ring subject to the proviso that at least one of the carbon atoms to which $R^{9'}$ and $R^{10'}$ are attached is saturated;

$R^6$, $R^7$ and $R^8$ are the same or different and are independently selected from the group consisting of $C_1$-$C_{20}$ aliphatic, $C_1$-$C_{20}$ heteroaliphatic, $C_3$-$C_{20}$ cycloaliphatic, $C_2$-$C_{20}$ heterocycloaliphatic, $C_5$-$C_{20}$ aryl, $C_3$-$C_{20}$ heteroaryl, and combinations thereof; and n is 1-5;

2) the second compound is an aldehyde or ketone of the formula:

wherein:

$R^1$ and $R^2$ are the same or different and are independently selected from the group consisting of H, $C_1$-$C_{20}$ aliphatic, $C_1$-$C_{20}$ heteroaliphatic, $C_3$-$C_{20}$ cycloaliphatic, $C_2$-$C_{20}$ heterocycloaliphatic, $C_5$-$C_{20}$ aryl, $C_3$-$C_{20}$ heteroaryl, and combinations thereof; or $R^1$ and $R^2$ together with the carbon to which they are attached define a $C_3$-$C_{20}$ cycloaliphatic ring, or a $C_2$-$C_{20}$ heterocycloaliphatic ring; and 3) the bifunctional organocatalyst is selected from the group consisting of:

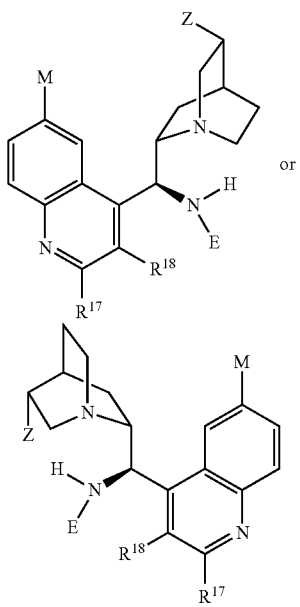

or

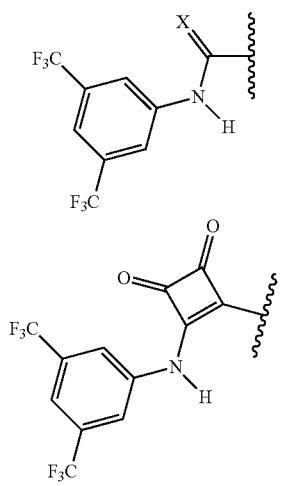

wherein

Z is $C_1$-$C_5$ aliphatic optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide and combinations thereof;

M is selected from the group consisting of H, OH, SH, O($C_1$-$C_5$ aliphatic), and S($C_1$-$C_5$ aliphatic);

$R^{17}$ and $R^{18}$ are the same or different and are independently selected from the group consisting of H, $C_3$-$C_{10}$ branched aliphatic, $C_3$-$C_{10}$ branched heteroaliphatic, $C_3$-$C_{20}$ cycloaliphatic, $C_2$-$C_{20}$ heterocycloaliphatic, $C_5$-$C_{20}$ aryl, $C_3$-$C_{20}$ heteroaryl, Br, I and combinations thereof; or $R^{17}$ and $R^{18}$ together with the carbon atoms to which they are attached define a monocyclic or polycyclic structure selected from the group consisting of $C_3$-$C_{20}$ cycloaliphatic, $C_2$-$C_{20}$ heterocycloaliphatic, $C_5$-$C_{20}$ aryl, $C_3$-$C_{20}$ heteroaryl; and E is a moiety selected from the group consisting of:

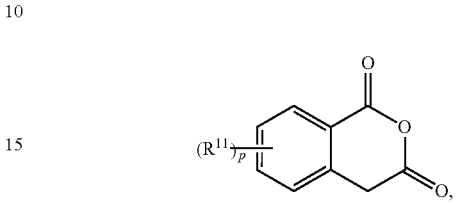

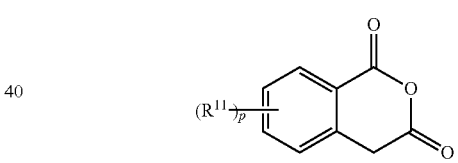

wherein X can be O or S.

Additionally, with reference to the embodiment comprising elements 1)-3) supra the method may be carried out in an ethereal solvent, for example $C_2$-$C_{12}$ ethers (cyclic and acyclic) such as diethylether, THF, 2-methyl THF, diisopropylether, methyltertbutylether (MTBE) and combinations thereof.

Desirably, item 1) of the embodiment comprising elements 1)-3) supra is a homophthalic anhydride derivative of the formula:

wherein $R^{11}$ and p are as defined above.

Desirably, item 2) of the embodiment comprising elements 1)-3) supra is an aldehyde of the formula:

$$R^1 \text{—CHO}$$

wherein:

$R^1$ is selected from the group consisting of $C_1$-$C_{20}$ aliphatic, $C_1$-$C_{20}$ heteroaliphatic, $C_3$-$C_{20}$ cycloaliphatic, $C_2$-$C_{20}$ heterocycloaliphatic, $C_5$-$C_{20}$ aryl, $C_3$-$C_{20}$ heteroaryl, and combinations thereof.

Advantageously, when:

i) The enolisable $C_4$-$C_{50}$ cyclic organic is of the general formula:

wherein $R^{11}$ and p are as defined above; and ii) the second compound is an aldehyde or ketone of the formula:

wherein:

$R^1$ and $R^2$ are the same or different and are independently selected from the group consisting of H, $C_1$-$C_{20}$ aliphatic, $C_1$-$C_{20}$ heteroaliphatic, $C_3$-$C_{20}$ cycloaliphatic, $C_2$-$C_{20}$ heterocycloaliphatic, $C_5$-$C_{20}$ aryl, $C_3$-$C_{20}$ heteroaryl, and combinations thereof; or $R^1$ and $R^2$ together with the carbon to which they are attached define a $C_3$-$C_{20}$ cycloaliphatic ring, or a $C_2$-$C_{20}$ heterocycloaliphatic ring, the method of the present invention provides a facile enantioselective route to chiral dihydroisocoumarins.

The present inventors have also found a number of new cinchona alkaloid molecules that show excellent catalytic activity in the synthetic method of the present invention.

Accordingly, in a further aspect, the present invention provides for a compound of the general formula (Ia) or (Ib):

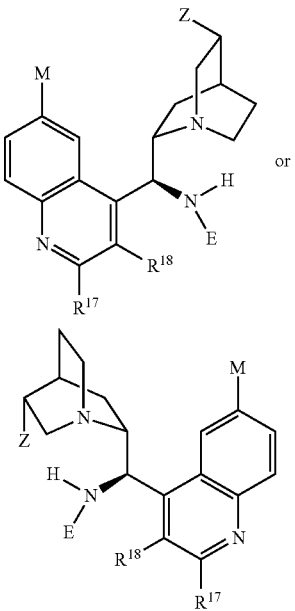

wherein

Z is $C_1$-$C_5$ aliphatic optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide and combinations thereof;

M is selected from the group consisting of H, OH, SH, O($C_1$-$C_5$ aliphatic), and S($C_1$-$C_5$ aliphatic);

$R^{17}$ and $R^{18}$ are the same or different and are independently selected from the group consisting of H, $C_3$-$C_{10}$ branched aliphatic, $C_3$-$C_{10}$ branched heteroaliphatic, $C_3$-$C_{20}$ cycloaliphatic, $C_2$-$C_{20}$ heterocycloaliphatic, $C_5$-$C_{20}$ aryl, $C_3$-$C_{20}$ heteroaryl, Br, I and combinations thereof, subject to the proviso that only one of $R^{17}$ and $R^{18}$ can be H; or $R^{17}$ and $R^{18}$ together with the carbon atoms to which they are attached may define a monocyclic or polycyclic structure selected from the group consisting of $C_3$-$C_{20}$ cycloaliphatic, $C_2$-$C_{20}$ heterocycloaliphatic, $C_5$-$C_{20}$ aryl, $C_3$-$C_{20}$ heteroaryl; and E is a moiety selected from the group consisting of:

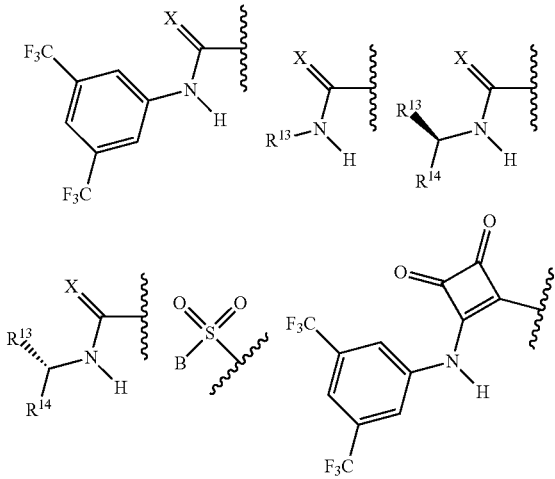

-continued

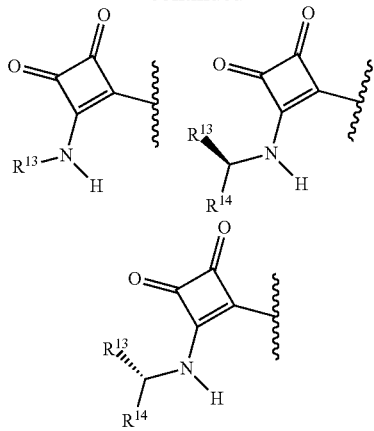

wherein X can be O or S;

B is selected from the group consisting of $C_1$-$C_{20}$ aliphatic, $C_1$-$C_{20}$ heteroaliphatic, $C_3$-$C_{20}$ cycloaliphatic, $C_2$-$C_{20}$ heterocycloaliphatic, $C_5$-$C_{20}$ aryl, $C_3$-$C_{20}$ heteroaryl, and combinations thereof optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof;

$R^{13}$ and $R^{14}$ are the same or different and are independently selected from the group consisting of $C_1$-$C_{20}$ aliphatic, $C_1$-$C_{20}$ heteroaliphatic, $C_3$-$C_{20}$ cycloaliphatic, $C_2$-$C_{20}$ heterocycloaliphatic, $C_5$-$C_{20}$ aryl, $C_3$-$C_{20}$ heteroaryl, and combinations thereof optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof; or $R^{13}$ and $R^{14}$ together with the carbon atom to which they are attached define a $C_3$-$C_{20}$ cycloaliphatic ring, $C_2$-$C_{20}$ heterocycloaliphatic ring, $C_5$-$C_{20}$ aryl ring, $C_3$-$C_{20}$ heteroaryl ring optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof.

Advantageously, molecules according to the present invention possessing a non-H substituent at one of $R^{17}$ and $R^{18}$ show excellent asymmetric induction when utilised as catalysts in the synthetic method of the present invention. In particular, molecules of the present invention possessing a non-H substituent at one of $R^{17}$ and $R^{18}$ when used as catalysts in the method of the present invention were found to afford end products with an enantiomeric excess of up to 99%.

In one embodiment, the compound of the present invention is:

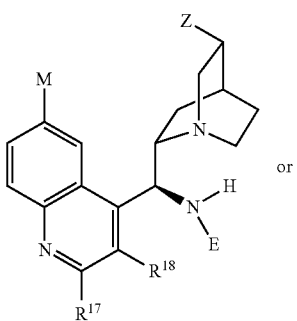

-continued

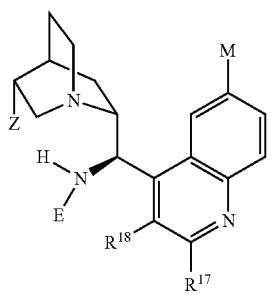

wherein

Z is $C_1$-$C_5$ aliphatic optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide and combinations thereof;

M is selected from the group consisting of H, OH, SH, O($C_1$-$C_5$ aliphatic), and S($C_1$-$C_5$ aliphatic);

$R^{17}$ and $R^{18}$ are the same or different and are independently selected from the group consisting of H, $C_3$-$C_{10}$ branched aliphatic, $C_3$-$C_{10}$ branched heteroaliphatic, $C_3$-$C_{20}$ cycloaliphatic, $C_2$-$C_{20}$ heterocycloaliphatic, $C_5$-$C_{20}$ aryl, $C_3$-$C_{20}$ heteroaryl, Br, I and combinations thereof, subject to the proviso that only one of $R^{17}$ and $R^{18}$ can be H; or $R^{17}$ and $R^{18}$ together with the carbon atoms to which they are attached may define a monocyclic or polycyclic structure selected from the group consisting of $C_3$-$C_{20}$ cycloaliphatic, $C_2$-$C_{20}$ heterocycloaliphatic, $C_5$-$C_{20}$ aryl, $C_3$-$C_{20}$ heteroaryl; and E is a moiety selected from the group consisting of:

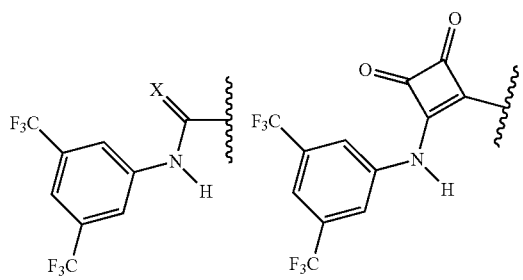

wherein X is O or S.

The compound of the present invention may be:

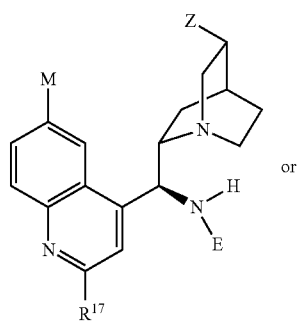

-continued

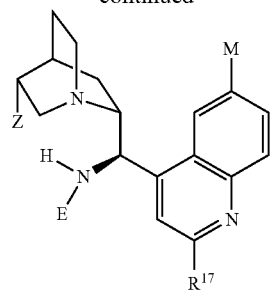

wherein

Z is $C_1$-$C_5$ aliphatic optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide and combinations thereof;

M is selected from the group consisting of H, OH, SH, O($C_1$-$C_5$ aliphatic), and S($C_1$-$C_5$ aliphatic);

$R^{17}$ is selected from the group consisting of $C_3$-$C_{10}$ branched aliphatic, $C_3$-$C_{10}$ branched heteroaliphatic, $C_3$-$C_{20}$ cycloaliphatic, $C_2$-$C_{20}$ heterocycloaliphatic, $C_5$-$C_{20}$ aryl, $C_3$-$C_{20}$ heteroaryl, Br, I and combinations thereof, and E is a moiety selected from the group consisting of:

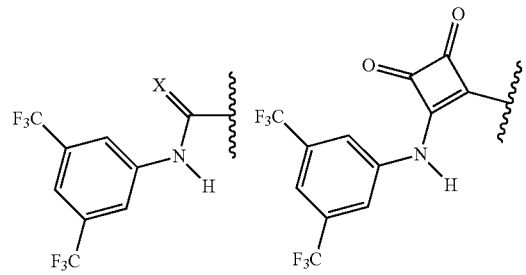

wherein X is O or S.

The compound of the present invention may be:

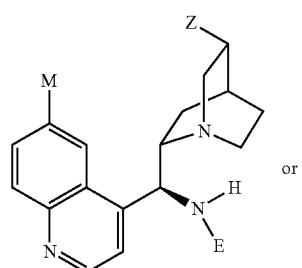

or

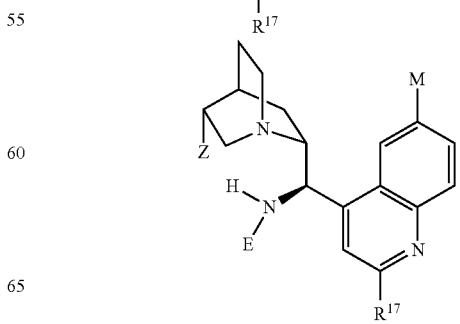

wherein

Z is $C_1$-$C_5$ aliphatic optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide and combinations thereof;

M is selected from the group consisting of H, OH, and $O(C_1$-$C_5$ aliphatic);

$R^{17}$ is selected from the group consisting of $C_5$-$C_{20}$ aryl, and $C_3$-$C_{20}$ heteroaryl; and E is a moiety selected from the group consisting of:

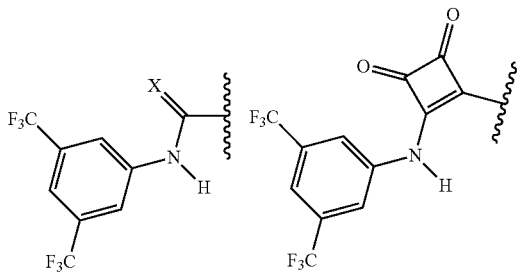

wherein X is O or S.

The compound of the present invention may be immobilised on a solid phase support or a magnetic nanoparticle. Advantageously, this may allow for automated combinatorial or high throughput applications utilising the compounds of the present invention.

In a further aspect, the present invention provides for use of a compound of the present invention as a catalyst in a chemical reaction. For example, the catalyst may be an asymmetric catalyst for imparting enantioselectivity to a synthetic reaction process.

As used herein, the term $C_x$-$C_y$ aliphatic refers to linear, branched, saturated and unsaturated hydrocarbon chains comprising $C_x$-$C_y$ carbon atoms (and includes $C_x$-$C_y$ alkyl, $C_x$-$C_y$ alkenyl and $C_x$-$C_y$ alkynyl). Similarly, references to $C_x$-$C_y$ alkyl, $C_x$-$C_y$ alkenyl and $C_x$-$C_y$ alkynyl include linear and branched $C_x$-$C_y$ alkyl, $C_x$-$C_y$ alkenyl and $C_x$-$C_y$ alkynyl.

As used herein, the term "$C_x$-$C_y$ cycloaliphatic" refers to unfused, fused, spirocyclic, polycyclic, saturated and unsaturated hydrocarbon rings comprising $C_x$-$C_y$ carbon atoms (and includes $C_x$-$C_y$ cycloalkyl, $C_x$-$C_y$ cycloalkenyl and $C_x$-$C_y$ cycloalkynyl).

The terms heteroaliphatic and heterocycloaliphatic embrace compounds of the above definitions, but where the carbon atoms of the hydrocarbon chains and hydrocarbon rings, respectively, are interspaced one or more times with at least one O, N or S.

As used herein, the term aryl/aromatic refers to an aromatic carbocyclic structure which is monocyclic or polycyclic, and which is unfused or fused. As used herein, the term heterocycle refers to cyclic compounds having as ring members atoms of at least two different elements. The cyclic compounds may be monocyclic or polycyclic and unfused or fused. As used herein, the term heteroaromatic/heteroaryl refers to an aromatic heterocyclic structure having as ring members atoms of at least two different elements. The aromatic heterocycle may be monocyclic or polycyclic and unfused or fused.

Where suitable, it will be appreciated that all optional and/or preferred features of one embodiment of the invention may be combined with optional and/or preferred features of another/other embodiment(s) of the invention.

DETAILED DESCRIPTION OF THE INVENTION

It should be readily apparent to one of ordinary skill in the art that the examples disclosed herein below represent generalised examples only, and that other arrangements and methods capable of reproducing the invention are possible and are embraced by the present invention.

In preliminary experiments, the results of which are given in Table 1, the addition of homophthalic anhydride (8) to benzaldehyde (9) was evaluated in THF at ambient temperature in the presence of a wide range of chiral alkaloid-derived catalysts 11 at 5 mol % loading. In the absence of catalyst, the reaction proceeds very slowly, with moderate diastereoselectivity in favour of anti-10 (entry 1).

Use of Hünig's base as a catalyst led to considerably faster reactions with no improvement in diastereoselectivity, however it was pleasing to observe that sub-stoichiometric catalysis of this reaction by an amine base was possible (entry 2). Both the parent cinchona alkaloid, quinine (11a), and its O-benzoylated derivative 11b promoted the reaction with marginally higher diastereoselectivity, however the product enantiomeric excesses were inadequate for synthetic utility (entries 3-4), as were those obtained from reactions catalysed by both the mono- and bifunctional C-9 arylated alkaloids 11c and 11d (entries 5-6). The bifunctional sulfonamide-substituted catalysts 11e-g, which have proven highly efficacious in the catalysis of asymmetric additions to anhydrides promoted the formation of predominantly anti-10 in excellent yield, with poor-moderate levels of enantioselectivity (entries 7-9). The exchange of the sulfonamide for urea- and thiourea functionality (i.e., catalysts 11h-l) resulted in higher enantioselectivity, with the thiourea-based catalyst 11l clearly superior to the others in this subset of the library (>75% ee for both the syn and anti diastereomers, with a 9 fold preference for the anti-stereoisomer, entries 10-14). The recently developed C-5' substituted alkaloid derivative 11m is a relatively poor catalyst from a stereoselectivity perspective (entry 15).

Squaramide-substituted catalysts, for example 11n could catalyse the formation of anti-10 with good diastereoselectivity and 90% ee (entry 16). The C2-symmetric analogue 11o, is unsuitable for use in the reaction currently under study (entry 17). The squaramide 11n proved the most promising of the known materials screened, yet did not represent an optimal catalytic solution. An analysis of molecular models led us to speculate that this may be due to the catalyst's quinoline ring being responsible for occupying two of the four quadrants defining the 3-dimensional space around the squaramide moiety. If one considers rotation around the single bond at the quinoline C-4 position, it is clear that the occupation of these quadrants is asymmetric, depending on whether the methoxy-substituted portion of the quinoline ring is orientated either towards the N—H bonds or the carbonyl moieties. To address this putative design-flaw, we installed a phenyl substituent at C-2, so that the steric requirement of the quinoline ring is more appropriately balanced, which we proposed would render catalyst performance less dependent on the orientation of this heterocyclic substituent.

TABLE 1

Catalyst evaluation and optimisation of the reaction conditions

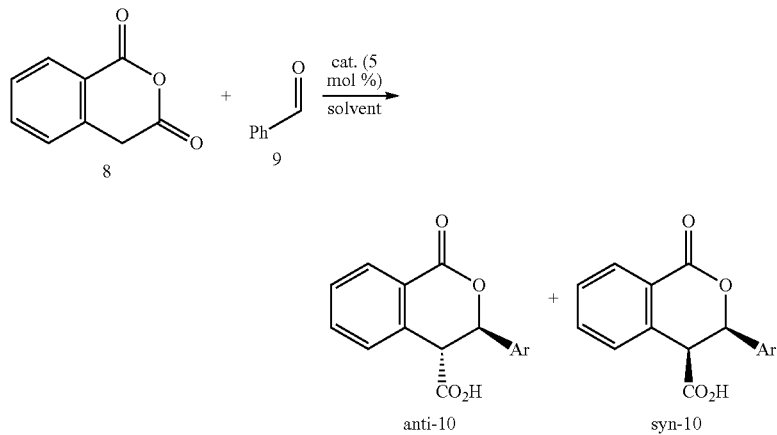

| Entry | Catalyst | Time (h) | Solvent | Conc. (M) | Temp. (° C.) | Yield (%)[a] | dr[b] | ee$_{syn}$ (%)[c] | ee$_{anti}$ (%)[c] |
|---|---|---|---|---|---|---|---|---|---|
| 1 | — | 19 | THF | 0.2 | rt | 20 | 75:25 | — | — |
| 2 | i-Pr$_2$NEt | 19 | THF | 0.2 | rt | 95 | 75:25 | — | — |
| 3 | 11a | 19 | THF | 0.2 | rt | 84 | 81:19 | 26 | −7 |
| 4 | 11b | 19 | THF | 0.2 | rt | 93 | 83:17 | −1 | −28 |
| 5 | 11c | 19 | THF | 0.2 | rt | 99 | 68:32 | −3 | 1 |
| 6 | 11d | 19 | THF | 0.2 | rt | 93 | 78:22 | −3 | −21 |
| 7 | 11e | 19 | THF | 0.2 | rt | 98 | 90:10 | 30 | 5 |
| 8 | 11f | 19 | THF | 0.2 | rt | 97 | 91:9 | 35 | −69 |
| 9 | 11g | 19 | THF | 0.2 | rt | 98 | 85:15 | 24 | −21 |
| 10 | 11h | 19 | THF | 0.2 | rt | 96 | 85:15 | 40 | 72 |
| 11 | 11i | 19 | THF | 0.2 | rt | >99 | 83:17 | 51 | 58 |
| 12 | 11j | 19 | THF | 0.2 | rt | 97 | 86:14 | 70 | 66 |
| 13 | 11k | 19 | THF | 0.2 | rt | 92 | 85:15 | 68 | 62 |
| 14 | 11l | 19 | THF | 0.2 | rt | 92 | 90:10 | 76 | 79 |
| 15 | 11m | 19 | THF | 0.2 | rt | 82 | 76:24 | −20 | 10 |
| 16 | 11n | 19 | THF | 0.2 | rt | 80 | 84:16 | 67 | 90 |
| 17 | 11o | 19 | THF | 0.2 | rt | 86 | 78:22 | 32 | 40 |
| 18 | 11p | 24 | THF | 0.2 | rt | 96 | 91:9 | 65 | 93 |
| 19 | 11p | 18 | THF | 0.1 | 23 | 98 | 91:9 | 73 | 94 |
| 20 | 11p | 18 | MTBE | 0.1 | 23 | >99 | 92:8 | 61 | 95 |
| 21 | 11p | 36 | CH$_2$Cl$_2$ | 0.1 | 23 | 57 | 82:18 | n.d.[d] | n.d.[d] |
| 22 | 11p | 18 | PhMe | 0.1 | 23 | >99 | 90:10 | 26 | 87 |
| 23 | 11p | 36 | MeCN | 0.1 | 23 | 65 | 72:28 | n.d.[d] | n.d.[d] |
| 24 | 11p | 20 | THF | 0.01 | rt | 97 | 82:18 | 92 | 91 |
| 25 | 11p | 36 | THF | 0.1 | 0 | 87 | 93:7 | n.d.[d] | 96 |
| 26 | 11p | 36 | MTBE | 0.1 | 0 | >99 | 95:5 | n.d.[d] | 96 |
| 27 | 11p | 22 | MTBE | 0.1 | −15 | 98 | 96:4 | n.d.[d] | 97 | catalysts

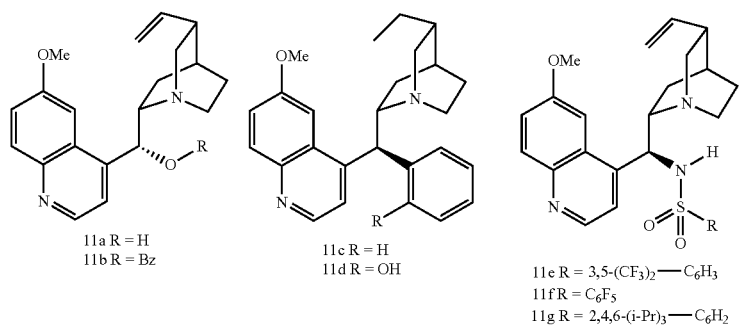

11a R = H
11b R = Bz

11c R = H
11d R = OH

11e R = 3,5-(CF$_3$)$_2$—C$_6$H$_3$
11f R = C$_6$F$_5$
11g R = 2,4,6-(i-Pr)$_3$—C$_6$H$_2$

TABLE 1-continued

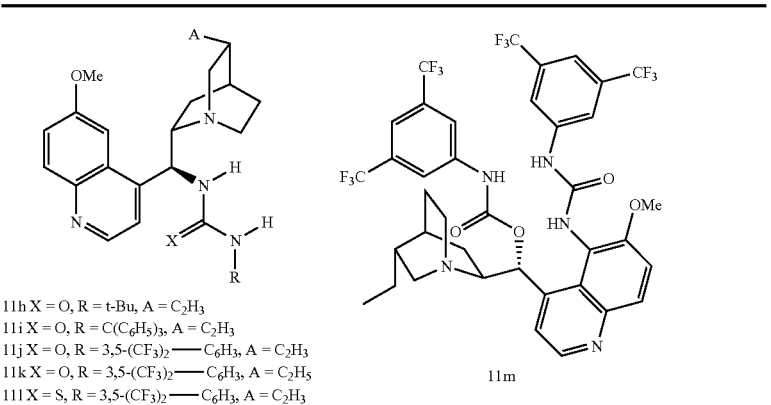

11h X = O, R = t-Bu, A = C₂H₃
11i X = O, R = C(C₆H₅)₃, A = C₂H₃
11j X = O, R = 3,5-(CF₃)₂—C₆H₃, A = C₂H₃
11k X = O, R = 3,5-(CF₃)₂—C₆H₃, A = C₂H₅
11l X = S, R = 3,5-(CF₃)₂—C₆H₃, A = C₂H₃

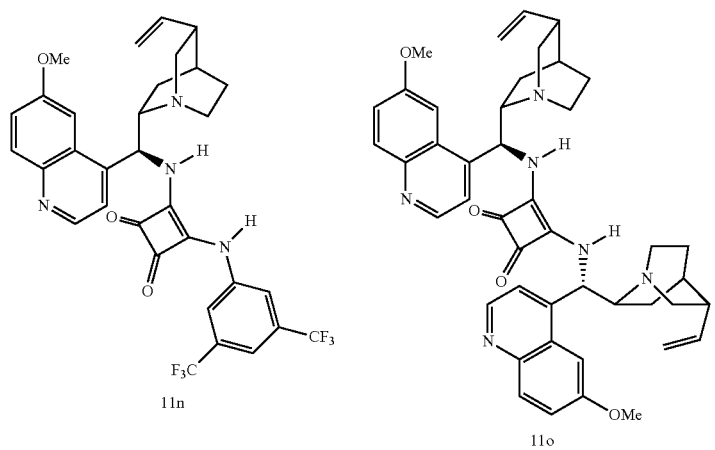

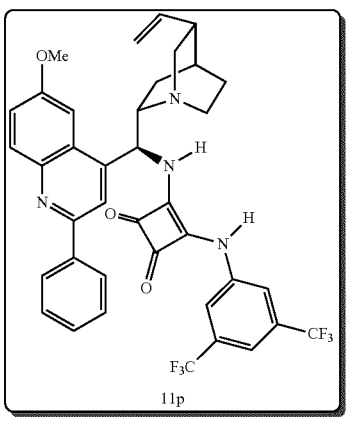

[a] Determined by ¹H NMR spectroscopy using 4-iodoanisole as an internal standard.
[b] Diastereomeric ratio (determined by ¹H NMR spectroscopy).
[c] Determined by CSP-HPLC.
[d] Not determined.

Use of this novel C-2 substituted catalyst 11p resulted in considerably improved product yield, enantio- and diastereoselectivity (entry 18). Further optimisation (entries 19-27) led to the identification of 2 sets of reaction conditions which allow the synthesis of anti-10 in ≥98% yield, ≥95:5 dr and ≥96% ee at convenient catalyst loading, reaction concentration and temperatures (entries 26 and 27).

TABLE 2
Evaluation of substrate scope: aldehyde component
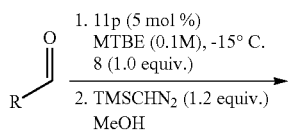
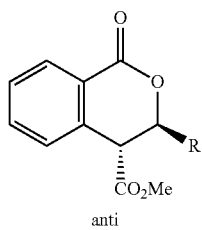
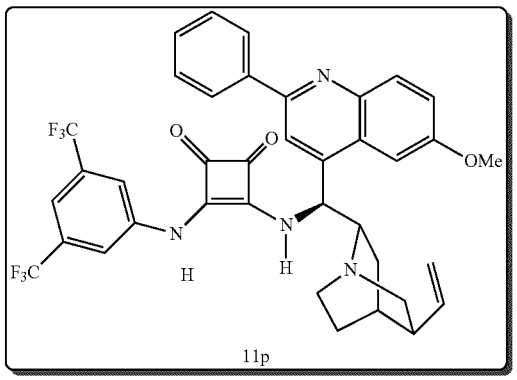
| Entry | Product | Time (h) | Yield (%)[a] of anti-diastereomer | dr[b] | ee (%)[c] |
|---|---|---|---|---|---|
| 1 | anti-12 (3-Cl-C6H4) | 48 | 93 (97)[d] | 97:3 | 96 |
| 2 | anti-13 (4-Cl-C6H4) | 40 | 93 (100)[d] | 95:5 | 95 |
| 3 | anti-14 (4-Br-C6H4) | 48 | 93 (100)[d] | 95:5 | 97 |
| 4 | anti-15 (4-NO2-C6H4) | 48 | 92 (100)[d] | 93:7 | 96 |

TABLE 2-continued
Evaluation of substrate scope: aldehyde component
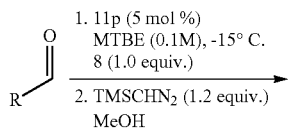
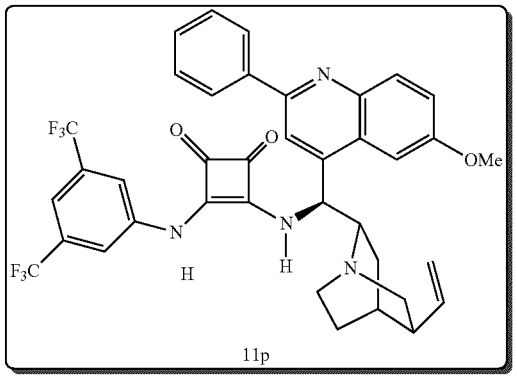
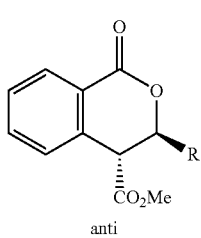
anti
| Entry | Product | Time (h) | Yield (%)[a] of anti-diastereomer | dr[b] | ee (%)[c] |
|---|---|---|---|---|---|
| 5 | anti-16 | 115 | 78 (90)[d] | 90:10 | 91 |
| 6 | anti-17 | 48 | 95 (100)[d] | 97:3 | 99 |
| 7 | anti-18 | 48 | 84 (90)[d] | 94:6 | 97 |
| 8 | anti-19 | 48 | 90 (98)[d] | 93:7 | 98 |

TABLE 2-continued

Evaluation of substrate scope: aldehyde component

Reaction scheme:
R–CHO
1. 11p (5 mol %), MTBE (0.1M), −15° C., 8 (1.0 equiv.)
2. TMSCHN$_2$ (1.2 equiv.), MeOH
→ anti product (isochroman-1-one with R and CO$_2$Me substituents)

Catalyst 11p: squaramide-derived bifunctional organocatalyst bearing a 3,5-bis(trifluoromethyl)phenyl group and a 2-phenyl-6-methoxyquinoline-substituted cinchona alkaloid moiety.

| Entry | Product | Time (h) | Yield (%)[a] of anti-diastereomer | dr[b] | ee (%)[c] |
|---|---|---|---|---|---|
| 9 | anti-20 (3-phenethyl isochromanone, MeO$_2$C) | 22 | 94[d] (100)[d] | 75:25 | 98 (90)[f] |
| 10[g] | anti-21 (3-cyclohexyl isochromanone, MeO$_2$C) | 93 | 98[d] (99)[d] | 78:22 | 98 (97)[f] |

[a] Isolated yield of the anti-diastereomer after column chromatography.
[b] Diastereomeric ratio (determined by $^1$H NMR spectroscopy).
[c] Determined by CSP-HPLC.
[d] Yield of the combined diastereomers prior to chromatography ($^1$H NMR spectroscopy) in parenthesis.
[e] Diastereomers inseparable: combined isolated yield.
[f] ee of syn-isomer in parenthesis.
[g] At −30° C.

Table 2 illustrates the range of substrates compatible with the method of the present invention. The methodology proved extraordinarily robust: when reacted in a 1:1 ratio with anhydride 8, electron-deficient- (entries 1-4), electron-rich- (entry 5) hindered- (entry 6) and heterocyclic aromatic (entries 7 and 8) aldehydes were well tolerated by the catalyst at just 5 mol % loading. Yields and enantiomeric excesses of the isolated anti-diastereomers 12-19 (to facilitate isolation and separation of the diastereomers the crude acids were esterified in situ upon completion of the reaction) were generally excellent (≥92% yield and ≥95% ee respectively). The deactivated p-anisaldehyde proved a greater challenge than the other electrophiles evaluated in this study (entry 5), yet this could still be obtained in good yield and >90% ee.

It should perhaps also be noted that thiophene carbaldehyde also proved a relatively difficult substrate, resulting in an 84% isolated yield (97% ee, entry 7) of 18. Aliphatic aldehydes also undergo the formal cycloaddition—both straight-chain (entry 9) and more hindered 'branched' aldehydes (entry 10) could be converted to 20 and 21 respectively. While the dr is uniformly excellent in the case of aromatic aldehydes, the use of aliphatic aldehydes leads to acceptable but elevated levels of the syn-diastereomer. This is somewhat mitigated by the fact that the anti-diastereomer is formed in both cases in near optical purity; in addition, the ee of the formed syn-diastereomer is also good-excellent.

TABLE 3

Evaluation of substrate scope: homophthalic anhydride component 1. 11p (5 mol %) MTBE (0.1M), -15° C. anhydride (1.0 equiv.)
2. TMSCHN₂ ⁱPrOH/THF 0° C.

| Entry | Product | Time (h) | Yield (%)[a] of anti-diastereomer | dr[b] | ee (%)[c] |
|-------|---------|----------|-----------------------------------|-------|-----------|
| 1 | anti-22 | 96 | 63 (87)[d] | 94:6 | 91 |
| 2 | anti-23 | 64 | 68 (95)[d] | 95:5 | 93 |
| 3 | anti-24 | 164 | 65 (81)[d] | 95:5 | 96 |

[a]Isolated yield of the anti-diastereomer after column chromatography.
[b]Diastereometric ratio (determined by ¹H NMR spectroscopy).
[c]Determined by CSP-HPLC.
[d]Yield (determined by ¹H NMR spectroscopy using an internal standard) of the anti-diastereomer prior to esterification and chromatography in parenthesis.

TABLE 4

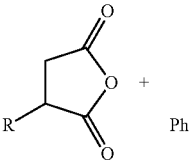

| Anhydride | Cat. | Temp. | Time | Conv.[a] | dr (cis:trans) | ee cis (Major) |
|---|---|---|---|---|---|---|
| 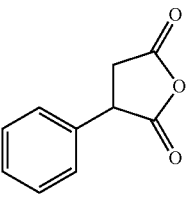 [SMILES: O=C1CC(c2ccccc2)C(=O)O1] | DIPEA 20 mol % | rt | 23 h | 71% | 89:11 | — |
|  | 11p | rt | 24 h | 44% | 90:10 | 68% |
|  | 11p | rt | 7 d | 66% | 88:12 | 64% |
|  | 11p | −15° C. | 110 h | 34% | 97:3 | 83% |
|  | 11p | −30° C. | 110 h | 17% | >99% | 83% |
| 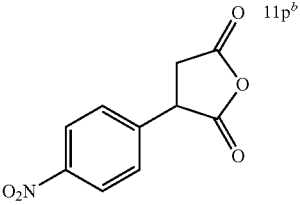 | 11p[b] | rt | 41 h | 94% | 93:7 | 74% |
| (3,5-dibromophenyl succinic anhydride) | 11p | −15° C. | 97 | 76 | 94:6 | 78 |

[a] conversion determined using $^1$H-NMR and p-iodoanisole (0.5 equiv.) as an internal standard.
[b] THF was added just before the NMR sample was taken to solubilise all the compounds.

Substitution at the aromatic ring is a feature of several of the medicinally relevant bicyclic dihydroisocoumarin compounds, and the scope of the present invention in this regard is evaluated in Table 3. Deactivating nitro- (entry 1) and bromo- (entry 2) functional groups can be used to form 22 and 23 respectively in excellent dr and ee. While the yield of the crude acids (determined by $^1$H NMR spectroscopy using an internal standard) was excellent in both cases, isolation of these lactones is more difficult due to ring-opening of the (now more electrophilic) lactones upon both on esterification and during careful column chromatography to separate the diastereomeric products. Nonetheless synthetically useful yields of pure anti-22 and 23 can be obtained. The electron-donating methoxy group was also found to be compatible—anti-24 was prepared in good yield and excellent ee (entry 3, Table 3).

The scope of the anhydride component in the synthetic method of the present invention is further investigated in Tables 4 and 5. A wide range of succinic anhydride derivatives show good to excellent ee.

TABLE 5
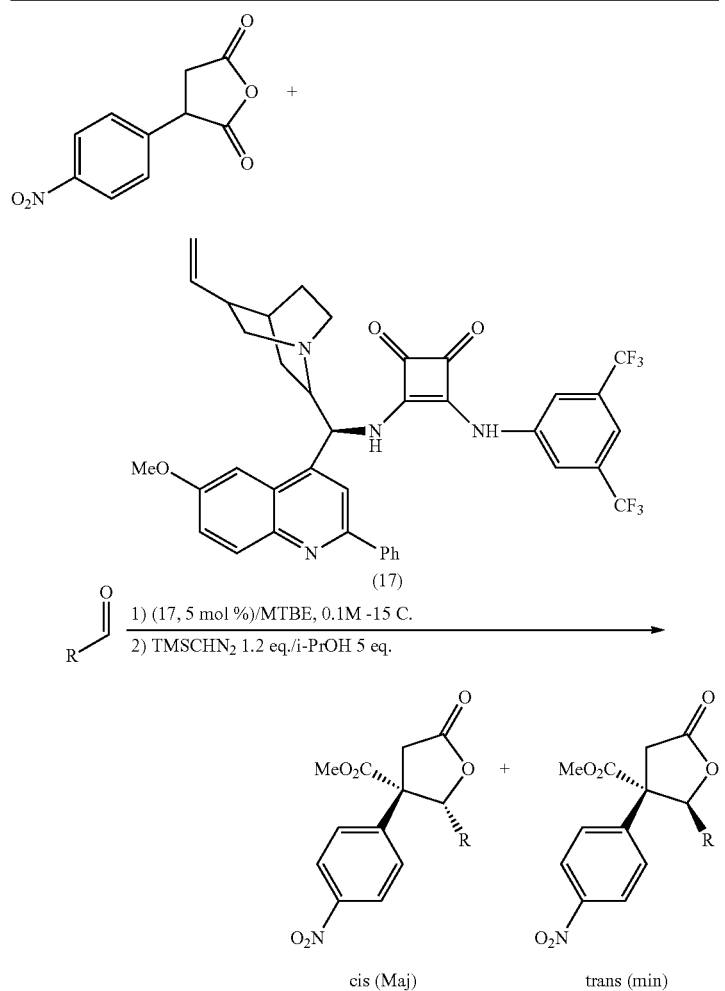
| Aldehyde | Time (h) | Conv.ᵃ | dr (cis:trans) | ee cis (Maj) |
|---|---|---|---|---|
| benzaldehyde | 164 | 98 | 97:3 | 86% |
| 4-Cl-benzaldehyde | 100 | 100 | 95:5 | 82% |
| 4-Br-benzaldehyde | 97 | 99 | 94:6 | 77% |
| 4-MeO-benzaldehyde | 164 (250) | 76 (81) | 92:8 | 73% |

TABLE 5-continued

| Aldehyde | | | | |
|---|---|---|---|---|
| 2-methylbenzaldehyde | 161 (250) | 65 (70) | 95:5 | 91% |
| 3-phenylpropanal | 100 | 100 | 72:28 | 95% |
| 2-thiophenecarboxaldehyde | 161 | 94 | 98:2 | 91% |
| 2-furaldehyde | 98 | 99 | >98:2 | 99% |
| cyclohexanecarboxaldehyde | 98[b] | 68 | 88:12 | 98 |

[a]conversion determined using using $^1$H-NMR and either p-iodoanisole or styrene (0.5 equiv.) as an internal standard
[b]Using 20 mol % of catalyst 11p.

General Procedure for the Preparation of Dihydroisocoumarins Anti-12 to Anti-21

A oven-dried 10 mL reaction vessel containing a stirring bar under argon atmosphere was charged with homophthalic anhydride (8) (39.9 mg, 0.246 mmol). Anhydrous MTBE (2.4 mL, 0.1 M) was added via syringe followed by the relevant aldehyde (0.246 mmol). N,N-Diisopropylethylamine (8.6 mL, 0.049 mmol-20 mol %) was added via syringe and the resulting mixture was stirred for 20 h at room temperature. To the reaction mixture containing the corresponding carboxylic acids, anhydrous MeOH (750 mL), followed by trimethylsilyldiazomethane (2.0 M solution in diethyl ether, 150 mL, 0.300 mmol) were added via syringe and the reaction was allowed to stir for 30 min. at room temperature. The solvent was then removed in vacuo and the crude mixture of diastereomeric esters was purified by flash chromatography to isolate the major diastereomer. In the case of dihydroisocoumarins synthesised with aliphatic aldehydes, both diastereomers were recovered combined after purification by column chromatography.

General Procedure for the Preparation of Dihydroisocoumarins Anti-22 to Anti-24

A oven-dried 10 mL reaction vessel containing a stirring bar under argon atmosphere was charged with the relevant homophthalic anhydride (0.246 mmol). Anhydrous MTBE (2.4 mL, 0.1 M) was added via syringe followed by benzaldehyde (25 mL, 0.246 mmol). The reaction was cooled to 0° C. and N,N-diisopropylethylamine (2.2 mL, 0.012 mmol-5 mol %) was added via syringe. For the synthesis of anti-24, N,N-diisopropylethylamine (8.6 ml, 0.049 mml-20 mol %) was used. The reaction was stirred for 20 at room temperature then it was diluted with EtOAc (15 mL) and extracted with an aqueous solution of NaHCO$_3$ (10% w/v, 3×15 mL). The combined aqueous extracts were acidified with HCl (2.0 N), a white precipitate formed and the mixture was then extracted with EtOAc (3×15 mL). The organic extracts were dried over MgSO$_4$ and the solvent was removed in vacuo to yield the diastereomeric mixture of carboxylic acids as an off-white solid. The acids were then dissolved in THF (0.1 M) and the solution was cooled to 0° C. Anhydrous isopropyl alcohol (5.0 equiv.) immediately followed by trimethylsilyldiazomethane (2.0 M solution in diethyl ether, 5.0 equiv.) were added via syringe and the reaction was allowed to stir for 1 h at room temperature. The solvent was then removed in vacuo at room temperature and the crude mixture of diastereomeric esters was purified by flash chromatography to isolate the major diastereomer.

Synthesis of Catalyst 11p

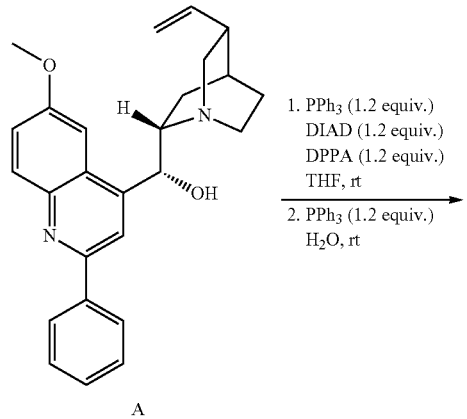

A

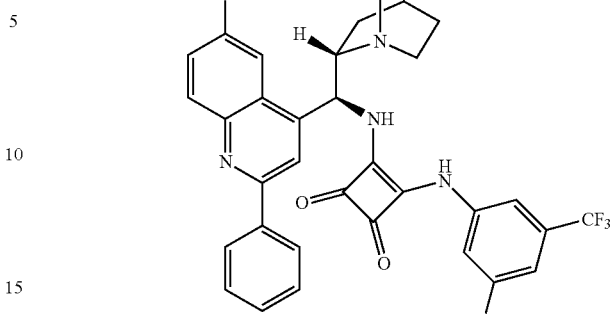

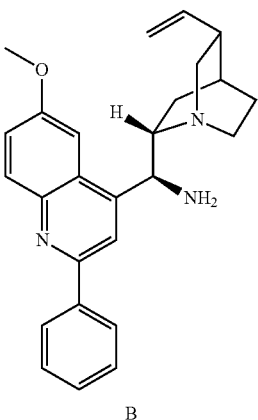

B

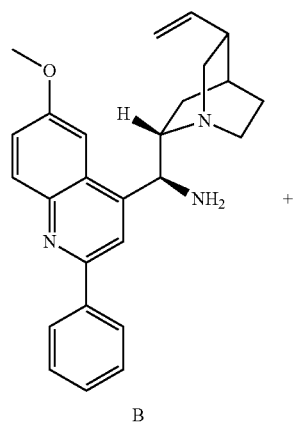

B +

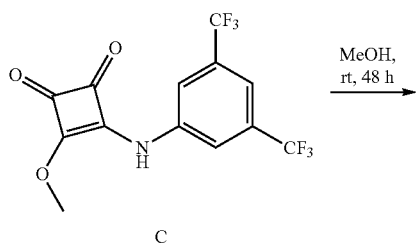

C (S)-[6-Methoxy-2-phenylquinolin-4-yl][(2S,4S,8R)-8-vinylquinuclidin-2-yl]methanamine Diisopropyl azodicarboxylate (DIAD) (1.65 mL, 8.4 mmol) was added to a stirred solution of A (2.8 g, 7.0 mmol) and triphenylphosphine (2.20 g, 8.4 mmol) in dry THF (50.0 mL) at 0° C. via syringe under an argon atmosphere in a 100 mL round-bottomed flask. After 30 min. diphenylphosphoryl azide (DPPA) (1.8 mL, 8.4 mmol) was added dropwise via syringe and the reaction mixture was stirred at 0° C. to rt for 16 h, then heating at 50° C. for 2 h. Triphenylphosphine (2.20 g, 8.4 mmol) was added portionwise and heating was maintained for 2 h. After cooling the reaction mixture to room temperature, water (10.0 mL) was added and the mixture stirred for 4 h. The THF was removed in vacuo and the residue was dissolved in HCl (2 N, 20.0 mL) and washed with CH2Cl2 (3×20.0 mL). The aqueous layer was basified with NaOH (2 N) and extracted with CH2Cl2 (4×10.0 mL), the combined organic extracts were dried over MgSO4 and the solvent removed in vacuo to yield a viscous pale yellow oil (2.46 g, 88%). Spectral data for this compound were consistent with those in the literature. $[\alpha]^{20}_{589}$=+30.3 (c=0.70, CHCl$_3$); $^1$H NMR (400 MHz, CDCl$_3$): δ=8.18 (d, J=7.4 Hz, 2H), 8.14 (d, J=9.3 Hz, 1H), 8.02 (br. s, 1H), 7.68 (br. s, 1H), 7.55 (app. t, 2H), 7.47 (t, J=7.4 Hz, 1H), 7.42 (dd, J=9.3, 2.6 Hz, 1H), 5.83-5.76 (m, 1H), 5.04-4.97 (m, 2H), 4.68 (br. s, 1H), 4.01 (s, 3H), 3.36-3.10 (m, 3H), 2.31 (br. s, 1H), 2.05 (br. s, 2H), 1.68-1.56 (m, 3H), 1.51-1.40 (m, 1H), 0.90-0.84 (m, 1H); HRMS (ESI): calcd. for [M+H]+C$_{26}$H$_{30}$N$_{3}$O requires 400.2389. found 400.2382.

3-[3,5-bis(Trifluoromethyl)phenylamino]-4-[(S)-[6-methoxy-2-phenylquinolin-4-yl][(2S,4S,8R)-8-vinylquinuclidin-2-yl]methylamino]cyclobut-3-ene-1,2-dione (11p)

To a stirred solution of B (1.50 g, 3.8 mmol) in methanol (10.0 mL) under an argon atmosphere was added a solution of C (1.25 g, 3.7 mmol) in methanol (10.0 mL) via syringe. The resultant mixture was stirred at room temperature for 48 h. The solvent was removed in vacuo and the residue dissolved in CH$_2$Cl$_2$ (20.0 mL). The product was precipitated using hexanes and collected by filtration to yield a white solid (2.20 g, 85%).

M.p. 192° C. (decomposition); $[\alpha]^{20}_{589}$=+115.8 (c=0.50, MeOH); $^1$H NMR (400 MHz, DMSO-d$^6$ 100° C.): δ=8.24 (d, J=7.4 Hz, 2H), 8.14 (s, 1H), 8.06 (d, J=9.2 Hz, 1H), 7.98 (s, 2H), 7.81 (d, J=2.6 Hz, 1H), 7.61-7.45 (m, 5H), 6.07 (d, J=11.0 Hz, 1H), 5.95 (ddd, J=17.4, 10.4, 7.1 Hz, 1H), 5.05 (d, J=17.4 Hz, 1H), 5.00 (d, J=10.4 Hz, 1H), 4.03 (s, 3H), 3.65-3.58 (m, 1H), 3.43-3.21 (m, 2H), 2.94-2.67 (m, 2H), 2.35 (m, 1H), 1.75-1.47 (m, 4H), 0.89 (m, 1H); 13C NMR (100 MHz, DMSO-d$^6$): δ=185.3, 180.6, 169.1, 163.3, 158.5, 154.2, 145.2, 144.7, 142.5, 141.2, 139.1, 132.2, 131.7 (q, J$_{C-F}$=32.8 Hz), 129.7, 129.2, 127.5, 127.0, 123.7, 123.6 (q, J$_{C-F}$=273.3 Hz), 118.8, 117.2, 115.2, 114.6, 101.9, 59.4, 56.1, 55.9, 53.9, 40.6, 39.9, 31.4, 27.6, 26.2; IR (neat): 3520, 295.3, 1791, 1687, 1599, 1546, 1476, 1438, 1377, 1274, 1235, 1174, 1133, 1030, 997, 929, 879, 835, 695 cm$^{-1}$; HRMS (ESI): calcd. for [M+H]+C$_{38}$H$_{33}$N$_4$O$_3$F$_6$ requires 707.2450. found 707.2457.
Catalyst Evaluation at Low Temperature (General Procedures)
Catalyst Evaluation at Low Temperature—Table 2 (General Procedure A)

A oven-dried 10 mL reaction vessel containing a stirring bar under argon atmosphere was charged with homophthalic anhydride (8) (39.9 mg, 0.246 mmol) and catalyst 11p (8.7 mg, 0.012 mmol-5 mol %). Anhydrous MTBE (2.4 mL, 0.1 M) was added via syringe and the reaction mixture was then cooled to −15° C. The relevant aldehyde (0.246 mmol) was added via syringe and the resulting mixture was stirred for the time indicated in Table 2. The yield and diastereomeric ratio of the products were monitored by $^1$H-NMR spectroscopic analysis using p-iodoanisole (28.8 mg, 0.123 mmol) as an internal standard. To the reaction mixture containing the corresponding carboxylic acids, anhydrous MeOH (750 mL), followed by trimethylsilyldiazomethane (2.0 M solution in diethyl ether, 150 mL, 0.300 mmol) were added via syringe and the reaction was allowed to stir for 30 min. at room temperature. The solvent was then removed in vacuo and the crude mixture of diastereomeric esters was purified by flash chromatography eluting in gradient from 100% hexanes to 5% EtOAc in hexanes to isolate the major diastereomer. The enantiomeric excess of the products was determined by CSP-HPLC using the conditions indicated for each case.
Catalyst Evaluation at Low Temperature Using Substituted Homophthalic Anhydrides—Table 3 (General Procedure B)

A oven-dried 10 mL reaction vessel containing a stirring bar under argon atmosphere was charged with the relevant homophthalic anhydride (0.246 mmol). Anhydrous MTBE (2.4 mL, 0.1 M) was added via syringe and the reaction mixture was then cooled to −15° C. Freshly distilled benzaldehyde (25.0 ml, 0.246 mmol) was added via syringe followed by catalyst 11p (8.7 mg, 0.012 mmol-5 mol %) and the resulting mixture was stirred for the time indicated in Table 3. The yield and diastereomeric ratio of the products were monitored by 1H-NMR spectroscopic analysis using p-iodoanisole (28.8 mg, 0.123 mmol) as an internal standard. The reaction was then diluted with EtOAc (15 mL) and extracted with an aqueous solution of NaHCO$_3$ (10% w/v, 3×15 mL). The combined aqueous extracts were acidified with HCl (2.0 N), a white precipitate formed and the mixture was then extracted with EtOAc (3×15 mL). The combined organic extracts were dried over MgSO4 and the solvent was removed in vacuo to yield the diastereomeric mixture of carboxylic acids. The acids were then dissolved in THF (0.1 M) and the solution was cooled to 0° C. Anhydrous isopropyl alcohol (5.0 equiv.) immediately followed by trimethylsilyldiazomethane (2.0 M solution in diethyl ether, 5.0 equiv.) were added via syringe and the reaction was allowed to stir for 1 h at room temperature. The solvent was then removed in vacuo at room temperature and the crude mixture of diastereomeric esters was purified by flash chromatography eluting in gradient from 100% hexanes to 5% EtOAc in hexanes to isolate the major diastereomer. The enantiomeric excess of the products was determined by CSP-HPLC using the conditions indicated for each case.

Reductive debromination of anti-14 and assignment of the absolute configuration of anti-10

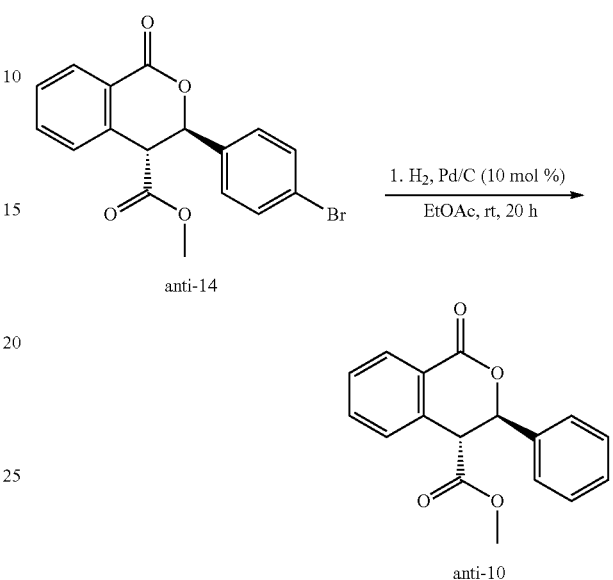

A 25 mL round-bottomed flask containing a stirring bar was charged with anti-14 (20.2 mg, 0.0559 mmol) and EtOAc (10.0 mL). 10% Pd/C (2 mol %) was added, the flask was evacuated, placed under an atmosphere of hydrogen gas at atmospheric pressure and stirred for 20 h at room temperature. The flask was then evacuated and filled with an inert atmosphere. The reaction mixture was filtered through a pad of Celite and washed with EtOAc as the eluent. The solvent was removed in vacuo and the residue was purified by column chromatography (10% EtOAc in hexanes) to afford a mixture of anti-10 and anti-14. Since the absolute configuration of anti-14 was known, this allowed the assignment of the absolute configuration of anti-10 as (R,R) through comparison of the HPLC chromatogram from the reaction above with that of anti-10 derived from the addition of homophthalic anhydride to benzaldehyde in the presence of 11p (Table 1).

Synthesis of Homophthalic Anhydrides

Homophthalic Anhydride (8)

A 100 mL round-bottomed flask containing a stirring bar was charged with homophthalic acid (2.0 g, 11.101 mmol). Acetic anhydride (25.0 mL) was added, the flask was fitted with a condenser and the reaction mixture was heated at 80° C. for 2 h. The excess acetic anhydride was removed in vacuo and the solid obtained was triturated with Et$_2$O (10.0 mL), filtered and dried to obtain homophthalic anhydride as an off white solid (1.53 g, 85%). Spectral data for this compound were consistent with those in the literature. M.p. 140-144° C. (lit. m.p. 140-145° C.); 1H NMR (400 MHz, DMSO-d$_6$): δ=8.05 (d, J=8.2 Hz, 1H), 7.75 (app. t, 1H), 7.52 (app. t, 1H), 7.44 (d, J=7.8 Hz, 1H), 4.27 (s, 2H).

7-Nitroisochroman-1,3-dione

A oven-dried 10 mL round-bottomed flask containing a stirring bar was charged with 5-nitro-2-(carboxymethyl)benzoic acid (500 mg, 2.22 mmol). Freshly distilled acetyl chloride (5.0 ml) was added, the flask was fitted with a condenser and the reaction mixture was refluxed under an argon atmosphere for 16 h. The reaction was then cooled to room temperature and the excess acetyl chloride was removed in vacuo. The solid obtained was triturated with Et2O (5.0 mL), filtered and dried to give 7-nitroisochroman-1,3-dione as an off white solid (372.5 mg, 81%). Spectral data for this compound were consistent with those in the literature. M.p. 154-156° C. (lit. m.p. 154-155° C.); 1H NMR (400 MHz, DMSO-$d_6$): δ=8.67 (s, 1H), 8.54 (d, J=7.5 Hz, 1H), 7.72 (d, J=7.5 Hz, 1H), 4.41 (s, 2H).

7-Bromoisochroman-1,3-dione

A oven-dried 10 mL round-bottomed flask containing a stirring bar was charged with 5-bromo-2-(carboxymethyl) benzoic acid (500 mg, 1.93 mmol). Freshly distilled acetyl chloride (5.0 ml) was added, the flask was fitted with a condenser and the reaction mixture was refluxed under an argon atmosphere for 16 h. The reaction was then cooled to room temperature and the excess acetyl chloride was removed in vacuo. The solid obtained was triturated with Et2O (5.0 mL), filtered and dried to give 7-bromoisochroman-1,3-dione as an off white solid (404.7 mg, 87%). Spectral data for this compound were consistent with those in the literature. M.p. 176-178° C. (lit.7 M.p. 171-173° C.); 1H NMR (400 MHz, DMSO-$d_6$): δ=8.13 (s, 1H), 7.94 (d, J=8.2 Hz, 1H), 7.41 (d, J=8.2 Hz, 1H), 4.23 (s, 2H).

7-Methoxyisochroman-1,3-dione 2-(Carboxymethyl)-5-methoxybenzoic acid which is the precursor of 7-methoxyisochroman-1,3-dione was synthesised over 3 steps following essentially the procedures of Hill et al. (R. A. Hill, S. Rudra, B. Peng, D. S. Roane, J. K. Bounds, Y. Zhang, A. Adloo, T. Lu, *Bioorg. Med. Chem.* 2003, 11, 2099.) and Usgaonkar et al. (H. K. Desai, R. N. Usgaonkar, *J. Indian Chem. Soc.* 1963, 40, 239.) with some modifications (see below).

6-Methoxy-3-(trichloromethyl)isobenzofuran-1(3H)-one

A oven-dried 25 mL three neck round-bottomed flask containing a stirring bar was fitted with a drying tube ($CaCl_2$) and was charged with m-methoxybenzoic acid (5.04 g, 17.91 mmol) followed by chloral hydrate (2.96 g, 17.91 mmol). Concentrated $H_2SO_4$ (12.0 mL) was added and the reaction mixture was left stirring at room temperature for 24 h. It was then poured onto ice, a thick precipitate formed and the mixture was left stirring vigorously until the ice was dissolved. The precipitate was filtered, washed with water and dried. The solid was recrystallised from ethanol, the crystals were then filtered and dried to yield 6-methoxy-3-(trichloromethyl)isobenzofuran-1(3H)-one as off-white needles (3.16 g, 63%). Spectral data for this compound were consistent with those in the literature. M.p. 134-136° C. (lit. m.p. 136-137° C.); 1H NMR (400 MHz, DMSO-$d_6$): δ=7.88 (d, J=8.3 Hz, 1H), 7.49-7.39 (m, 2H), 6.54 (s, 1H), 3.90 (s, 3H).

2-(2,2-dichlorovinyl)-5-Methoxybenzoic acid

A 100 mL round-bottomed flask containing a stirring bar was charged with 6-methoxy-3-(trichloromethyl)isobenzofuran-1(3H)-one (3.09 g, 10.94 mmol) and glacial acetic acid (40.0 mL). Zinc dust (2.86 g, 43.76 mmol) was added in small portions over 30 min. to the stirred reaction mixture. The reaction was left stirring at room temperature for further 30 min. and then heated at reflux for 1 h. It was filtered hot over a pad of Celite and the filtrates were diluted with water. The precipitate formed was collected by filtration and recrystallised from EtOH/$H_2O$ to give 2-(2,2-dichlorovinyl)-5-methoxybenzoic acid as white needles (1.74 g, 64%). Spectral data for this compound were consistent with those in the literature. M.p. 164-166° C. (lit. m.p. 167-168° C.); 1H NMR (400 MHz, DMSO-$d_6$): δ=13.31 (br. s, 1H), 7.51 (d, J=8.7 Hz, 1H), 7.47-7.39 (m, 2H), 7.21 (dd, J=8.7 Hz, J=2.2 Hz, 1H), 3.82 (s, 3H).

2-(Carboxymethyl)-5-methoxybenzoic acid

A oven-dried 25 mL three neck round-bottomed flask containing a stirring bar was fitted with a drying tube ($CaCl_2$) and charged with concentrated $H_2SO_4$ (12.0 mL). Dichlorovinyl)-5-methoxybenzoic acid (1.69 g, 6.83 mmol) was added portion wise to the stirred solution over 20 min. so that each additional portion was added only after the previous one was completely dissolved. After the addition was complete the reaction was left stirring at room temperature for 2 h and then it was poured onto ice. A precipitate formed and the mixture was stirred until the ice was dissolved. The precipitate was filtered, washed with cold water and dried to give 2-(carboxymethyl)-5-methoxybenzoic acid as an off-white solid (1.18 g, 82%). Spectral data for this compound were consistent with those in the literature. M.p. 175-177° C. (lit. m.p. 180-182° C.); 1H NMR (400 MHz, DMSO-$d_6$): δ=12.36 (br. s, 2H), 7.39 (d, J=2.6 Hz, 1H), 7.24 (d, J=8.4 Hz, 1H), 7.08 (dd, J=8.4 Hz, J=2.6 Hz, 1H), 3.84 (s, 2H), 3.78 (s, 3H).

7-Methoxyisochroman-1,3-dione

The compound was synthesised as reported by Balci et al. (S. Ozcan, C. Dengiz, M. K. Deliömeroglu, E. Sahin, M. Balci, *Tetrahedron Lett.* 2011, 52, 1495) using 2-(carboxymethyl)-5-methoxybenzoic acid (1.14 g, 5.42 mmol). The crude product was purified by trituration with $Et_2O$ to afford 7-methoxyisochroman-1,3-dione as a yellow solid (861 mg, 83%). Spectral data for this compound were consistent with those in the literature. M.p. 138-140° C. (lit. m.p. 144-145° C.); 1H NMR (400 MHz, DMSO-$d_6$): δ=7.49 (d, J=2.1 Hz, 1H), 7.40-7.30 (m, 2H), 4.19 (s, 2H), 3.84 (s, 3H).

Characterisation Data (3R,4R)-Methyl 1-oxo-3-phenylisochroman-4-carboxylate (anti-10, Table 1, entry 27)

Prepared according to general procedure A using freshly distilled benzaldehyde (25.0 mL, 0.246 mmol). The reaction was stirred for 22 h to give a diastereomeric mixture of carboxylic acids in a 96:4 ratio. After esterification, the major diastereomer (anti-10) was isolated and purified by column chromatography to give a white solid (63.8 mg, 92%). CSP-HPLC analysis: Chiralcel OD-H (4.6 mm×25 cm), hexane/IPA: 83/17, 0.5 mL min-1, RT, UV detection at 254 nm, retention times: 96.5 min. (minor enantiomer) and 133.0 min. (major enantiomer). Spectral data for this compound were consistent with those in the literature. M.p. 118-120° C. (lit. m.p. 129-132° C.); TLC (hexanes:EtOAc, 8:2 v/v): Rf=0.34; $[α]^{20}_{589}$=+26.0 (c=0.20, $CHCl_3$); 1H NMR (400 MHz, $CDCl_3$): δ=8.19 (d, J=8.0 Hz, 1H), 7.60 (app. t, 1H), 7.49 (app. t, 1H), 7.44-7.30 (m, 5H), 7.20 (d, J=7.7 Hz, 1H), 5.86 (d, J=8.3 Hz, 1H), 4.35 (d, J=8.3 Hz, 1H), 3.69 (s, 3H); 13C NMR (151 MHz, CDCl3): δ=170.3, 164.1, 136.8, 136.3, 134.5, 130.8, 129.2, 129.0, 128.9, 126.92, 126.90, 124.8, 80.8, 52.8, 50.9; IR (neat): 2957, 1722, 1601, 1456, 1441, 1244, 1080, 997, 782, 701 cm−1; HRMS (ESI): calcd. for [M+Na]+ $C_{17}H_{14}O_4Na$ requires 305.0790. found 305.0805.

(3R,4R)-Methyl 3-(3-chlorophenyl)-1-oxoisochroman-4-carboxylate (anti-12, Table 2, entry 1)

Prepared according to general procedure A using freshly distilled 3-chlorobenzaldehyde (27.8 mL, 0.246 mmol). The reaction was stirred for 48 h to give a diastereomeric mixture of carboxylic acids in a 97:3 ratio. After esterification, the major diastereomer (anti-12) was isolated and purified by column chromatography to give an off-white solid (72.5 mg, 93%). CSP-HPLC analysis. Chiralcel OD-H (4.6 mm×25 cm), hexane/IPA: 83/17, 0.5 mL min-1, RT, UV detection at 254 nm, retention times: 31.6 min. (minor enantiomer) and 46.0 min. (major enantiomer). M.p. 70-72° C.; TLC (hexanes:EtOAc, 8:2 v/v): Rf=0.27; $[α]^{20}_{589}$=+31.0 (c=0.20, CHCl$_3$); 1H NMR (400 MHz, CDCl$_3$): δ=8.18 (d, J=7.5 Hz, 1H), 7.62 (app. t, 1H), 7.50 (app. t, 1H), 7.41 (s, 1H), 7.37-7.24 (m, 3H), 7.21 (d, J=7.5 Hz, 1H), 5.82 (d, J=8.5 Hz, 1H), 4.30 (d, J=8.5 Hz, 1H), 3.72 (s, 3H); $^{13}$C NMR (100 MHz, CDCl$_3$): δ=170.0, 163.8, 138.7, 135.9, 134.9, 134.7, 130.9, 130.2, 129.5, 129.1, 127.1, 126.8, 125.1, 124.4, 79.9, 52.9, 50.8; IR (neat): 3063, 2958, 2925, 2853, 1730, 1603, 1437, 1261, 1155, 1119, 1081, 784, 737, 708 cm−1; HRMS (ESI): calcd. for [M+H]+$C_{17}H_{14}O_4Cl$ requires 317.0581. found 317.0588.

(3R,4R)-Methyl 3-(4-chlorophenyl)-1-oxoisochroman-4-carboxylate (anti-13, Table 2, entry 2)

Prepared according to general procedure A using recrystallised 4-chlorobenzaldehyde (34.6 mg, 0.246 mmol). The reaction was stirred for 40 h to give a diastereomeric mixture of carboxylic acids in a 95:5 ratio. After esterification, the major diastereomer (anti-13) was isolated and purified by column chromatography to give a white solid (72.7 mg, 93%). CSP-HPLC analysis. Chiralcel OD-H (4.6 mm×25 cm), hexane/IPA: 99/1, 1.0 mL min-1, RT, UV detection at 254 nm, retention times: 77.7 min. (major enantiomer) and 94.2 min. (minor enantiomer). M.p. 95-97° C.; TLC (hexanes:EtOAc, 8:2 v/v): Rf=0.28; $[α]^{20}_{589}$=+16.0 (c=0.20, CHCl$_3$); 1H NMR (400 MHz, CDCl$_3$): δ=8.18 (d, J=7.7 Hz, 1H), 7.61 (app. t, 1H), 7.50 (app. t, 1H), 7.39-7.29 (m, 4H), 7.19 (d, J=7.7 Hz, 1H), 5.82 (d, J=8.7 Hz, 1H), 4.30 (d, J=8.7 Hz, 1H), 3.71 (s, 3H); $^{13}$C NMR (100 MHz, CDCl$_3$): δ=170.0, 163.9, 136.1, 135.3, 135.2, 134.7, 130.9, 129.12, 129.11, 128.4, 126.7, 124.5, 80.1, 52.9, 50.8; IR (neat): 2955, 2926, 2862, 1736, 1709, 1602, 1459, 1261, 1001, 826, 740, cm−1; HRMS (ESI): calcd. for [M+H]+$C_{17}H_{14}O_4Cl$ requires 317.0581. found 317.0572.

(3R,4R)-Methyl 3-(4-bromophenyl)-1-oxoisochroman-4-carboxylate (anti-14, Table 2, entry 3)

Prepared according to general procedure A using recrystallised p-bromobenzaldehyde (45.5 mg, 0.246 mmol). The reaction was stirred for 48 h to give a diastereomeric mixture of carboxylic acids in a 95:5 ratio. After esterification, the major diastereomer (anti-14) was isolated and purified by column chromatography to give a white solid (82.8 mg, 93%). CSP-HPLC analysis. Chiralcel OD-H (4.6 mm×25 cm), hexane/IPA: 99/1, 1.0 mL min-1, RT, UV detection at 254 nm, retention times: 83.3 min. (major enantiomer) and 102.6 min. (minor enantiomer). M.p. 138-140° C.; TLC (hexanes:EtOAc, 8:2 v/v): Rf=0.27; $[α]^{20}_{589}$=+8.0 (c=0.20, CHCl$_3$); 1H NMR (400 MHz, CDCl$_3$): δ=8.18 (d, J=7.8 Hz, 1H), 7.65-7.57 (app. t, 1H), 7.55-7.45 (m, 3H), 7.28 (d, J=7.2 Hz, 2H), 7.19 (d, J=7.5 Hz, 1H), 5.81 (d, J=8.4 Hz, 1H), 4.29 (d, J=8.4 Hz, 1H), 3.71 (s, 3H); $^{13}$C NMR (100 MHz, CDCl$_3$): δ=169.1, 163.8, 135.9, 135.7, 134.6, 132.0, 130.8, 129.1, 128.6, 126.7, 124.4, 123.3, 80.0, 52.9, 50.7; IR (neat): 3071, 3018, 2953, 1726, 1601, 1490, 1258, 1009, 822, 736, 692 cm−1; HRMS (ESI): calcd. for [M−H]+$C_{17}H_{12}O_4Br$ requires 358.9919. found 358.9910.

(3R,4R)-Methyl 3-(4-nitrophenyl)-1-oxoisochroman-4-carboxylate (anti-15, Table 2, entry 4)

Prepared according to general procedure A using recrystallised 4-nitrobenzaldehyde (37.2 mg, 0.246 mmol). The reaction was stirred for 48 h to give a diastereomeric mixture of carboxylic acids in a 93:7 ratio. After esterification, the major diastereomer (anti-15) was isolated and purified by column chromatography in gradient from 100% hexanes to 15% EtOAc in hexanes in 92% yield as a white solid (74.2 mg, 92%). CSP-HPLC analysis. Chiralcel OD-H (4.6 mm×25 cm), hexane/IPA: 90/10, 0.7 mL min-1, RT, UV detection at 254 nm, retention times: 97.6 min. (major enantiomer) and 133.0 min. (minor enantiomer). M.p. 131-133° C.; TLC (hexanes:EtOAc, 8:2 v/v): Rf=0.14; $[α]^{20}_{589}$=+22.0 (c=0.20, CHCl$_3$); 1H NMR (400 MHz, CDCl$_3$): δ=8.24 (d, J=8.6 Hz, 2H), δ 8.19 (d, J=7.8 Hz, 1H), 7.68-7.57 (m, 3H), 7.52 (app. t, 1H), 7.21 (d, J=7.8 Hz, 1H), 5.97 (d, J=8.3 Hz, 1H), 4.32 (d, J=8.3 Hz, 1H), 3.73 (s, 3H); $^{13}$C NMR (100 MHz, CDCl$_3$): δ=169.7, 163.4, 148.4, 143.7, 135.5, 134.9, 131.0, 129.4, 127.9, 126.8, 124.3, 124.1, 79.5, 53.1, 50.7; IR (neat): 3080, 2956, 2925, 2849, 1730, 1600, 1524, 1458, 1438, 1352, 1247, 1079, 1012, 859, 750, 693 cm−1; HRMS (ESI): calcd. for [M−H] $C_{17}H_{12}NO_6$ requires 326.0665. found 326.0674.

(3R,4R)-Methyl 3-(4-methoxyphenyl)-1-oxoisochroman-4-carboxylate (anti-16, Table 2, entry 5)

Prepared according to general procedure A using freshly distilled 4-methoxybenzaldehyde (29.8 mL, 0.246 mmol). The reaction was stirred for 115 h to give a diastereomeric mixture of carboxylic acids in a 90:10 ratio. After esterification, the major diastereomer (anti-16) was isolated and purified by column chromatography in gradient from 100% hexanes to 10% EtOAc in hexanes to give a white solid (60.1 mg, 78%). CSP-HPLC analysis. Chiralpak AD-H (4.6 mm×25 cm), hexane/IPA: 97/3, 1.0 mL min-1, RT, UV detection at 254 nm, retention times: 81.3 min. (minor enantiomer) and 89.5 min. (major enantiomer). M.p. 82-84° C.; TLC (hexanes:EtOAc, 8:2 v/v): Rf=0.20; $[α]^{20}_{589}$=+13.5 (c=0.20, CHCl$_3$); 1H NMR (400 MHz, CDCl$_3$): δ=8.18 (d, J=7.8 Hz, 1H), 7.60 (app. t, 1H), 7.49 (app. t, 1H), 7.31 (d, J=8.6 Hz, 2H), 7.19 (d, J=7.8 Hz, 1H), 6.88 (d, J=8.6 Hz, 2H), 5.77 (d, J=9.0 Hz, 1H), 4.34 (d, J=9.0 Hz, 1H), 3.80 (s, 3H), 3.69 (s, 3H); $^{13}$C NMR (100 MHz, CDCl$_3$): δ=170.3, 164.4, 160.2, 136.6, 134.5, 130.8, 128.9, 128.7, 128.5, 126.7, 124.7, 114.2, 80.7, 55.4, 52.8, 50.9; IR (neat): 3012, 2962, 2932, 2844, 1713, 1604, 1516, 1249, 990, 734 cm−1; HRMS (ESI): calcd. for [M+Na]+$C_{18}H_{16}O_5Na$ requires 335.0895. found 335.0905.

(3R,4R)-Methyl 1-oxo-3-o-tolylisochroman-4-carboxylate (anti-17, Table 2, entry 6)

Prepared according to general procedure A using freshly distilled 2-methylbenzaldehyde (28.4 mL, 0.246 mmol). The reaction was stirred for 48 h to give a diastereomeric mixture of carboxylic acids in a 97:3 ratio. After esterification, the major diastereomer (anti-17) was isolated and purified by column chromatography to give a white solid (69.4 mg, 95%) CSP-HPLC analysis. Chiralcel OD-H (4.6 mm×25 cm), hexane/IPA: 83/17, 0.5 mL min-1, RT, UV detection at 254 nm, retention times: 20.7 min. (minor enantiomer) and 31.8 min. (major enantiomer). M.p. 114-116° C.; TLC (hexanes:EtOAc, 8:2 v/v): Rf=0.33; $[\alpha]^{20}_{589}$=−20.0 (c=0.20, CHCl$_3$); 1H NMR (400 MHz, CDCl$_3$): δ=8.20 (d, J=7.7 Hz, 1H), 7.62 (app. t, 1H), 7.51 (app. t, 1H), 7.31 (d, J=7.3 Hz, 1H) 7.28-7.13 (m, 4H), 6.08 (d, J=8.7 Hz, 1H), 4.48 (d, J=8.7 Hz, 1H), 3.68 (s, 3H), 2.45 (s, 3H); $^{13}$C NMR (100 MHz, CDCl$_3$): δ=169.7, 163.8, 136.1 (2×C$_q$), 133.9, 133.7, 130.6, 130.3, 128.7, 128.4, 126.4, 126.2, 125.9, 124.1, 77.1, 52.2, 48.7, 18.9; IR (neat): 3073, 3027, 2955, 2932, 2846, 1720, 1602, 1459, 1434, 1253, 1003, 918, 741 cm−1; HRMS (ESI): calcd. for [M+Na]+O$_{18}$H$_{16}$O$_4$Na requires 319.0946. found 319.0946.

(3R,4R)-Methyl 1-oxo-3-(thiophen-2-yl)isochroman-4-carboxylate (anti-18, Table 2, entry 7)

Prepared according to general procedure A using freshly distilled 2-thiophenecarboxaldehyde (45.5 mL, 0.246 mmol). The reaction was stirred for 48 h to give a diastereomeric mixture of carboxylic acids in a 94:6 ratio. After esterification, the major diastereomer (anti-18) was isolated and purified by column chromatography to give a white solid (59.5 mg, 84%). CSP-HPLC analysis. Chiralcel OD-H (4.6 mm×25 cm), hexane/IPA: 90/10, 1.0 mL min-1, RT, UV detection at 254 nm, retention times: 32.7 min. (minor enantiomer) and 35.6 min. (major enantiomer). Spectral data for this compound were consistent with those in the literature. M.p. 110-112° C. (lit. m.p. 126-128° C.); TLC (hexanes:EtOAc, 8:2 v/v): Rf=0.25; $[\alpha]^{20}_{589}$=−68.0 (c=0.20, CHCl$_3$); 1H NMR (400 MHz, CDCl$_3$): δ=8.16 (d, J=7.9 Hz, 1H), 7.63 (app. t, 1H), 7.51 (app. t, 1H), 7.33-7.21 (m, 2H), 7.09-7.01 (m, 1H), 6.96-6.89 (m, 1H), 6.19 (d, J=6.1 Hz, 1H), 4.35 (d, J=6.1 Hz, 1H), 3.75 (s, 3H); 13C NMR (100 MHz, CDCl3): δ=169.8, 163.4, 139.6, 135.5, 134.4, 130.7, 129.2, 127.8, 127.3, 126.9, 126.8, 124.8, 76.4, 53.1, 50.5; IR (neat): 3104, 3011, 2951, 2925, 1727, 1703, 1605, 1459, 1431, 1359, 1332, 1226, 1081, 943, 714 cm−1; HRMS (ESI): calcd. for [M+H]+C$_{15}$H$_{13}$O$_4$S requires 289.0535. found 289.0527.

(3R,4R)-Methyl 3-(furan-2-yl)-1-oxoisochroman-4-carboxylate (anti-19, Table 2, entry 8)

Prepared according to general procedure A using freshly distilled furan-2-carboxaldehyde (20.4 mL, 0.246 mmol). The reaction was stirred for 48 h to give a diastereomeric mixture of carboxylic acids in a 93:7 ratio. After esterification, the major diastereomer (anti-19) was isolated and purified by column chromatography to give a yellow solid (61.4 mg, 90%). CSP-HPLC analysis. Chiralcel OD-H (4.6 mm×25 cm), hexane/IPA: 90/10, 1.0 mL min-1, RT, UV detection at 254 nm, retention times: 23.3 min. (major enantiomer) and 31.4 min. (minor enantiomer). M.p. 112-114° C.; TLC (hexanes:EtOAc, 8:2 v/v): Rf=0.24; $[\alpha]^{20}_{589}$=−70.0 (c=0.20, CHCl$_3$); 1H NMR (400 MHz, CDCl$_3$): δ=8.14 (d, J=7.8 Hz, 1H), δ 7.62 (app. t, 1H), 7.49 (app. t, 1H), 7.35 (s, 1H), 7.31 (d, J=7.4 Hz, 1H), 6.34-6.24 (m, 2H), 6.00 (d, J=5.9 Hz, 1H), 4.46 (d, J=5.9 Hz, 1H), 3.76 (s, 3H); $^{13}$C NMR (100 MHz, CDCl$_3$): δ=169.8, 163.5, 149.7, 143.4, 135.5, 134.4, 130.7, 129.1, 127.7, 124.6, 110.7, 109.8, 73.9, 53.2, 47.1; IR (neat): 3141, 3120, 2951, 2853, 1737, 1715, 1601, 1462, 1435, 1258, 1121, 1004, 930, 745, 690 cm−1; HRMS (ESI): calcd. for [M+H]+O$_{15}$H$_{13}$O$_5$ requires 273.0763. found 273.0774.

Methyl 1-oxo-3-phenethylisochroman-4-carboxylate (anti-20-syn-20, Table 2, entry 9)

Prepared according to general procedure A using freshly distilled hydrocinnamaldehyde (32.4 mL, 0.246 mmol). The reaction was stirred for 22 h to give a diastereomeric mixture of carboxylic acids in a 75:25 ratio. After esterification, both diastereomers (anti-20 and syn-20) were purified by column chromatography to give a pale yellow oil (71.7 mg, 94%, combined yield for both diastereoisomers). The diastereomeric ratio of the esters was found to be 79:21 (anti-20:syn-20) by 1H-NMR spectroscopic analysis. CSP-HPLC analysis. Chiralpak OJ-H (4.6 mm×25 cm), hexane/IPA: 80/20, 0.5 mL min-1, RT, UV detection at 254 nm, retention times: anti-20 52.6 min. (major enantiomer) and 76.2 min. (minor enantiomer); syn-20 66.5 min. (major enantiomer) and 106.6 min. (minor enantiomer). TLC (hexanes:EtOAc, 8:2 v/v): Rf=0.35; anti-20: $^1$H NMR (600 MHz, CDCl$_3$): δ=8.15 (d, J=7.8 Hz, 1H), 7.59 (app. t, 1H), 7.47 (app. t, 1H), 7.35-7.25 (m, 3H), 7.25-7.15 (m, 3H), 4.91-4.84 (m, 1H), 3.92 (d, J=6.8 Hz, 1H), 3.76 (s, 3H), 2.92-3.02 (m, 1H), 2.83-2.75 (m, 1H), 2.13-2.03 (m, 1H), 1.97-1.87 (m, 1H); 13C NMR (100 MHz, CDCl3): δ=170.6, 164.0, 140.6, 136.0, 134.3, 130.7, 128.9, 128.7, 128.6, 127.3, 126.40, 124.7, 78.3, 52.9, 48.7, 35.7, 31.3; syn-20: 1H NMR (600 MHz, CDCl3): δ=8.15 (d, J=7.9 Hz, 1H), 7.56 (app. t, 1H), 7.48 (app. t, 1H), 7.35-7.25 (m, 2H), 7.25-7.15 (m, 4H), 4.60-4.53 (m, 1H), 3.83 (d, J=3.2, 1H), 3.68 (s, 3H), 3.02-2.92 (m, 1H), 2.90-2.83 (m, 1H), 2.30-2.21 (m, 1H), 2.14-2.02 (m, 1H); $^{13}$C NMR (100 MHz, CDCl$_3$): δ=169.4, 164.8, 140.5, 136.8, 133.9, 130.9, 129.2, 128.8, 128.7, 127.4, 126.42, 125.5, 77.3, 52.8, 48.1, 34.5, 31.4; IR (neat): 3062, 3027, 2952, 2927, 2860, 1723, 1603, 1457, 1244, 1159, 1120, 1086, 700 cm−1; HRMS (ESI): calcd. for [M+Na]+O$_{19}$H$_{18}$O$_4$Na requires 333.1103. found 333.1103.

Methyl 3-cyclohexyl-1-oxoisochroman-4-carboxylate (anti-21-syn-21, Table 2, entry 10)

Prepared according to general procedure A using freshly distilled cyclohexanecarboxyaldehyde (29.8 mL, 0.246 mmol). The reaction was stirred for 93 h at −30° C. to give a diastereomeric mixture of carboxylic acids in a 78:22 ratio. After esterification, both diastereomers (anti-21 and syn-21) were purified by column chromatography to give a pale yellow oil (69.5 mg, 98%, combined yield for both diastereoisomers). The diastereomeric ratio of the esters was found to be 79:21 (anti-21:syn-21) by $^1$H-NMR spectroscopic analysis. CSP-HPLC analysis. Chiralcel OD-H (4.6 mm×25 cm), hexane/IPA: 60/40, 0.1 mL min-1, RT, UV detection at 254 nm, retention times: anti-21 47.1 min. (major enantiomer) and 57.7 min. (minor enantiomer); syn-21 55.4 min. (minor enantiomer) and 62.8 min. (major enantiomer). TLC (hexanes:EtOAc, 8:2 v/v): Rf=0.41; anti-21: $^1$H NMR (600 MHz, CDCl$_3$): δ=8.13 (d, J=6.9 Hz, 1H), 7.58 (app. t, 1H), 7.46 (app. t, 1H), 7.22 (d, J=7.7 Hz, 1H), 4.66 (app. t, 1H), 4.06 (d, J=5.8 Hz, 1H), 3.77 (s, 3H), 1.97-1.88 (m, 1H), 1.87-1.08 (m, 10H); $^{13}$C NMR (100 MHz, CDCl$_3$): δ=171.2, 164.1, 136.1, 134.2, 130.4, 128.8, 127.6, 125.1, 83.5, 52.9, 45.7, 40.5, 29.4, 27.9, 26.1, 26.0, 25.9; syn-21: $^1$H NMR (600 MHz, CDCl$_3$): δ=8.14 (d, J=6.9 Hz, 1H), 7.56 (app. t, 1H), 7.47 (app. t, 1H), 7.31 (d, J=7.5 Hz, 1H), 4.24 (dd, J=9.9, J=3.0, 1H), 4.00 (d, J=3.0 Hz, 1H), 3.66 (s, 3H), 2.41-2.23 (m, 1H), 2.03-1.97 (m, 1H), 1.87-1.08 (m, 7H), 1.08-0.95 (m, 2H); $^{13}$C NMR (100 MHz, CDCl$_3$): δ=169.5, 165.1, 137.1, 133.8, 130.8, 129.1, 127.4, 125.8, 83.3, 52.7, 46.0, 40.0, 29.6, 28.5, 26.3, 25.7, 25.3; IR (neat): 2927, 2854, 1723, 1604, 1459, 1240, 1160, 1113, 1082 cm-1; HRMS (ESI): calcd. for [M+H]+ C$_{17}$H$_{21}$O$_4$ requires 289.1440. found 289.1435.

(3R,4R)-Methyl 7-nitro-1-oxo-3-phenylisochroman-4-carboxylate (anti-22, Table 3, entry 1)

Prepared according to general procedure B using 7-nitroisochroman-1,3-dione (51.0 mg, 0.246 mmol) and freshly distilled benzaldehyde (25 mL, 0.246 mmol). The reaction was stirred for 96 h to give a diastereomeric mixture of carboxylic acids in a 92:8 ratio. After esterification, the major diastereomer (anti-22) was isolated and purified by a rapid column chromatography eluting in gradient from 20% EtOAc in hexanes to 30% EtOAc in hexanes to give a white solid (51.1 mg, 63%). CSP-HPLC analysis. Chiralcel OD-H (4.6 mm×25 cm), hexane/IPA: 90/10, 1.0 mL min-1, RT, UV detection at 254 nm, retention times: 110.6 min (minor enantiomer) and 122.8 min (major enantiomer). M.p. 148-150° C.; TLC (hexanes:EtOAc, 8:2 v/v): Rf=0.17; [α]$^{20}_{589}$=+31.0 (c=0.20, CHCl$_3$); $^1$H NMR (600 MHz, CDCl$_3$): δ=8.98 (d, J=2.1 Hz, 1H), 8.42 (dd, J=8.5 Hz, J=2.1 Hz, 1H), 7.45 (d, J=8.5 Hz, 1H), 7.41-7.29 (m, 5H), 5.98 (d, J=6.9 Hz, 1H), 4.43 (d, J=6.9 Hz, 1H), 3.73 (s, 3H); $^{13}$C NMR (151 MHz, CDCl$_3$): δ=169.1, 162.0, 148.4, 142.0, 136.0, 129.5, 129.4, 129.12, 128.6, 126.53, 126.50, 125.8, 80.5, 53.3, 50.4; IR (neat): 2956, 2923, 2853, 1745, 1718, 1614, 1530, 1439, 1349, 1259, 1160, 1125, 999, 911, 802, 740 cm-1; HRMS (ESI): calcd. for [M–H] C$_{17}$H$_{12}$NO$_6$ requires 326.0665. found 326.0665.

(3R,4R)-Methyl 7-bromo-1-oxo-3-phenylisochroman-4-carboxylate (anti-23, Table 3, entry 2)

Prepared according to general procedure B using 7-bromoisochroman-1,3-dione (59.3 mg, 0.246 mmol) and freshly distilled benzaldehyde (25 mL, 0.246 mmol). The reaction was stirred for 64 h to give a diastereomeric mixture of carboxylic acids in a 95:5 ratio. After esterification, the major diastereomer (anti-23) was isolated and purified by column chromatography to give a white solid (60.6 mg, 68%). CSP-HPLC analysis. Chiralcel OD-H (4.6 mm×25 cm), hexane/IPA: 90/10, 1.0 mL min-1, RT, UV detection at 254 nm, retention times: 26.9 min (minor enantiomer) and 43.9 min (major enantiomer). M.p. 132-134° C.; TLC (hexanes:EtOAc, 8:2 v/v): Rf=0.33; [α]$^{20}_{589}$=+29.0 (c=0.20, CHCl$_3$); 1H NMR (400 MHz, CDCl$_3$): δ=8.30 (s, 1H), 7.71 (d, J=8.1 Hz, 1H), 7.43-7.29 (m, 5H), 7.10 (d, J=8.3, 1H), 5.89 (d, J=7.6 Hz, 1H), 4.28 (d, J=7.6 Hz, 1H), 3.70 (s, 3H); $^{13}$C NMR (100 MHz, CDCl$_3$): δ=169.8, 162.8, 137.4, 136.4, 134.8, 133.5, 129.3, 129.0, 128.9, 126.7, 126.4, 122.9, 80.6, 53.0, 50.2; IR (neat): 2954, 2924, 2854, 1723, 1592, 1406, 1255, 1132, 1080, 997, 765 cm-1; HRMS (ESI): calcd. for [M+H]+ C$_{17}$H$_{14}$O$_4$Br requires 361.0075. found 361.0063.

(3R,4R)-Methyl 7-methoxy-1-oxo-3-phenylisochroman-4-carboxylate (anti-24, Table 3, entry 3)

Prepared according to general procedure B using 7-methoxyisochroman-1,3-dione (47.3 mg, 0.246 mmol) and freshly distilled benzaldehyde (25 mL, 0.246 mmol). The reaction was stirred for 164 h to give a diastereomeric mixture of carboxylic acids in a 95:5 ratio. After esterification, the major diastereomer (anti-24) was isolated and purified by column chromatography to give a white solid (52.3 mg, 68%). CSP-HPLC analysis. Chiralpak AD-H (4.6 mm×25 cm), hexane/IPA: 90/10, 1.0 mL min-1, RT, UV detection at 254 nm, retention times: 33.0 min (minor enantiomer) and 47.5 min (major enantiomer). M.p. 124-126° C.; TLC (hexanes: EtOAc, 8:2 v/v): Rf=0.31; [α]$^{20}_{589}$=+28.0 (c=0.20, CHCl$_3$); $^1$H NMR (400 MHz, CDCl$_3$): δ=7.66 (d, J=2.5 Hz, 1H), 7.43-7.30 (m, 5H), 7.20-7.06 (m, 2H), 5.86 (d, J=8.0 Hz, 1H), 4.28 (d, J=8.0 Hz, 1H), 3.87 (s, 3H), 3.69 (s, 3H); $^{13}$C NMR (100 MHz, CDCl$_3$): δ=170.5, 164.3, 159.9, 136.9, 129.2, 128.9, 128.29, 128.27, 126.8, 125.7, 122.3, 113.4, 80.9, 55.8, 52.8, 50.1; IR (neat): 2957, 2924, 2853, 1720, 1612, 1496, 1433, 1284, 1267, 1222, 1163, 1074, 1014, 877, 814, 740, 701 cm-1; HRMS (ESI): calcd. for [M–H] C18H15O5 requires 311.0919. found 311.0919.

CONCLUSION

The synthetic method of the present invention is extremely advantageous in that it is amenable to catalysis by bifunctional cinchona alkaloids at 5 mol % levels to generate a densely functionalised bicyclic heterocycles, for example a dihydroisocoumarin structure, with the formation of two new stereocentres in 98% yield, 97% ee and 96:4 dr under convenient conditions. The scope of the reaction is remarkably robust—electron rich, electron-deficient, hindered and heterocyclic aromatic aldehydes, in addition to both a-branched and unbranched aliphatic aldehydes are all compatible (with levels of product ee over 90% and usually between 95-99% and good to excellent diastereocontrol). Substitution on the anhydride component is also well tolerated by the catalyst.

The words "comprises/comprising" and the words "having/including" when used herein with reference to the present invention are used to specify the presence of stated features, integers, steps or components but do not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

The invention claimed is:

1. An enantioselective synthetic method for forming a lactone comprising the step of:
    reacting an enolisable C$_4$-C$_{50}$ cyclic organic anhydride with an aldehyde in the presence of a bifunctional organocatalyst;
    wherein the enolisable C$_4$-C$_{50}$ cyclic organic anhydride is selected from the group consisting of:

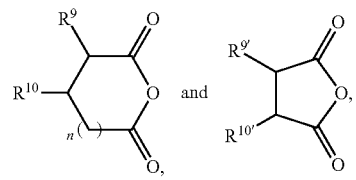

wherein,
R$^9$, R$^{9'}$, R$^{10}$ and R$^{10'}$ are the same or different and are independently selected from the group consisting of H, halogen, C≡N, NO$_2$, C$_1$-C$_5$ haloalkyl, C$_1$-C$_{20}$ aliphatic, C$_1$-C$_{20}$ heteroaliphatic, C$_3$-C$_{20}$ cycloaliphatic, C$_2$-C$_{20}$ heterocycloaliphatic, $C_5$-$C_{20}$ aryl, $C_3$-$C_{20}$ heteroaryl, $C(=O)OR^6$, $C(=O)NH_2$, $C(=O)NHR^6$, $C(=O)NR^6R^7$, $OR^6$, $OC(=O)R^6$, $OC(=O)OR^6$, $OC(=O)NH_2$, $OC(=O)NHR^6$, $OC(=O)NR^6R^7$, $N(H)C(=O)R^6$, $N(R^6)C(=O)R^7$, $N(H)C(=O)OR^6$, $N(R^6)C(=O)OR^7$, $N(H)C(=O)NH_2$, $N(R^6)C(=O)NH_2$, $N(H)C(=O)NHR^6$, $N(R^6)C(=O)NHR^7$, $N(H)C(=O)NR^6R^7$, $N(R^6)C(=O)NR^7R^8$, $S(=O)R^6$, $S(=O)_2R^6$, $P(=O)R^6R^7$, $P(=O)(OH)(OH)$, $P(=O)(OH)(OR^6)$, $P(=O)(OR^6)(OR^7)$; or $R^9$ and $R^{10}$ together with the carbon atoms to which they are attached define a $C_3$-$C_{20}$ cycloaliphatic ring, a $C_2$-$C_{20}$ heterocycloaliphatic ring, a $C_5$-$C_{20}$ aryl ring, or a $C_3$-$C_{20}$ heteroaryl ring; or $R^{9'}$ and $R^{10'}$ together with the carbon atoms to which they are attached define a $C_3$-$C_{20}$ cycloaliphatic ring, or a $C_2$-$C_{20}$ heterocycloaliphatic ring subject to the proviso that at least one of the carbon atoms to which $R^{9'}$ and $R^{10'}$ are attached is saturated;

$R^6$, $R^7$ and $R^8$ are the same or different and are independently selected from the group consisting of $C_1$-$C_{20}$ aliphatic, $C_1$-$C_{20}$ heteroaliphatic, $C_3$-$C_{20}$ cycloaliphatic, $C_2$-$C_{20}$ heterocycloaliphatic, $C_5$-$C_{20}$ aryl, $C_3$-$C_{20}$ heteroaryl, and combinations thereof; n is 1-5;

and wherein the bifunctional organocatalyst is selected from the group consisting of:

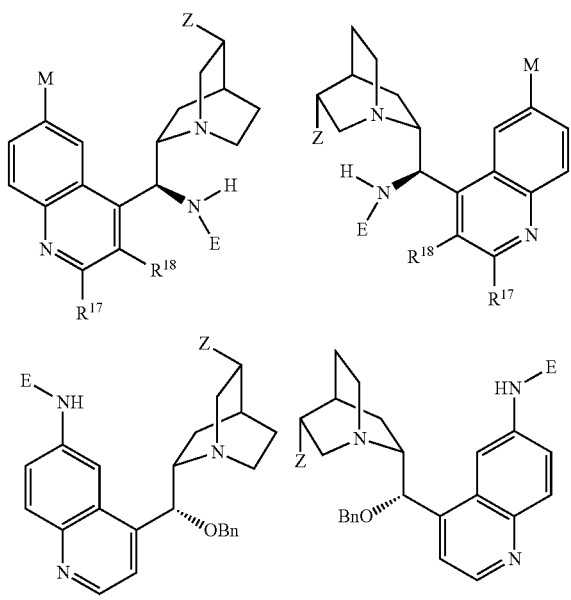

wherein

E is a moiety selected from the group consisting of:

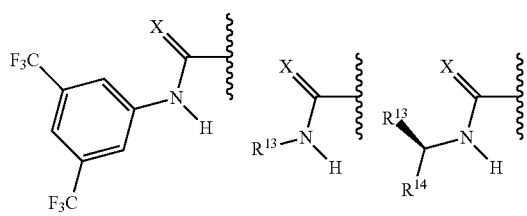

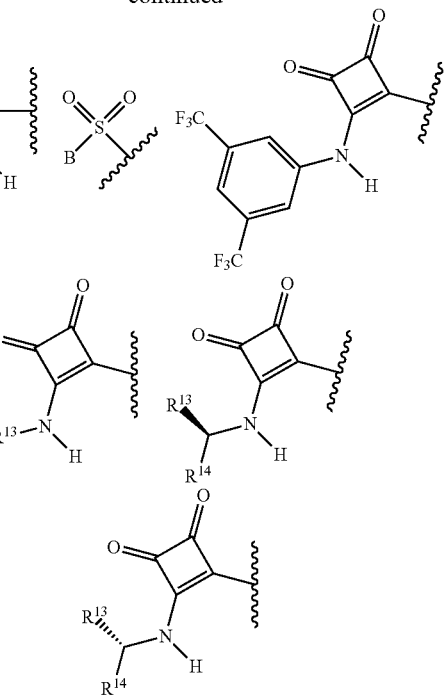

X is O or S;

M is selected from the group consisting of H, OH, SH, $O(C_1$-$C_5$ aliphatic), and $S(C_1$-$C_5$ aliphatic);

Z is $C_1$-$C_5$ aliphatic optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide and combinations thereof;

B is selected from the group consisting of $C_1$-$C_{20}$ aliphatic, $C_1$-$C_{20}$ heteroaliphatic, $C_3$-$C_{20}$ cycloaliphatic, $C_2$-$C_{20}$ heterocycloaliphatic, $C_5$-$C_{20}$ aryl, $C_3$-$C_{20}$ heteroaryl, and combinations thereof optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof;

$R^{17}$ and $R^{18}$ are the same or different and are independently selected from the group consisting of H, $C_3$-$C_{10}$ branched aliphatic, $C_3$-$C_{10}$ branched heteroaliphatic, $C_3$-$C_{20}$ cycloaliphatic, $C_2$-$C_{20}$ heterocycloaliphatic, $C_5$-$C_{20}$ aryl, $C_3$-$C_{20}$ heteroaryl, Br, I and combinations thereof; or $R^{17}$ and $R^{18}$ together with the carbon atoms to which they are attached define a monocyclic or polycyclic structure selected from the group consisting of $C_3$-$C_{20}$ cycloaliphatic, $C_2$-$C_{20}$ heterocycloaliphatic, $C_5$-$C_{20}$ aryl, $C_3$-$C_{20}$ heteroaryl;

$R^{13}$ and $R^{14}$ are the same or different and are independently selected from the group consisting of $C_1$-$C_{20}$ aliphatic, $C_1$-$C_{20}$ heteroaliphatic, $C_3$-$C_{20}$ cycloaliphatic, $C_2$-$C_{20}$ heterocycloaliphatic, $C_5$-$C_{20}$ aryl, $C_3$-$C_{20}$ heteroaryl, and combinations thereof optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof; or $R^{13}$ and $R^{14}$ together with the carbon atom to which they are attached define a $C_3$-$C_{20}$ cycloaliphatic ring, $C_2$-$C_{20}$ heterocycloaliphatic ring, $C_5$-$C_{20}$ aryl ring, $C_3$-$C_{20}$ heteroaryl ring optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof.

2. A method according to claim 1, wherein the aldehyde has the formula:

wherein

R$^1$ is selected from the group consisting of C$_1$-C$_{20}$ aliphatic, C$_1$-C$_{20}$ heteroaliphatic, C$_3$-C$_{20}$ cycloaliphatic, C$_2$-C$_{20}$ heterocycloaliphatic, C$_5$-C$_{20}$ aryl, C$_3$-C$_{20}$ heteroaryl, and combinations thereof; and R$^2$ is H.

3. A method according to claim 1, wherein the enolisable C$_4$-C$_{50}$ cyclic organic anhydride is of the general formula:

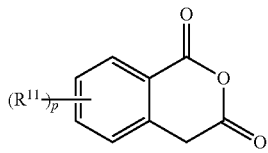

wherein p is 0-4;

each occurrence of R$^{11}$ is independently selected from the group consisting of C$_1$-C$_{10}$ aliphatic, C$_3$-C$_{10}$ cycloaliphatic C(=O)OR$^6$, C(=O)NH$_2$, C(=O)NHR$^6$, C(=O)NR$^6$R$^7$, OR$^6$, OC(=O) R$^6$, OC(=O)O R$^6$, OC(=O)NH$_2$, OC(=O)NHR$^6$, OC(=O)NR$^6$R$^7$, N(H)C(=O)R$^6$, N(R$^6$)C(=O)R$^7$, N(H)C(=O)OR$^6$, N(R$^6$)C(=O)OR$^7$, N(H)C(=O)NH$_2$, N(R$^6$)C(=O)NH$_2$, N(H)C(=O)NHR$^6$, N(R$^6$)C(=O)NHR$^7$, N(H)C(=O)NR$^6$R$^7$, N(R$^6$)C(=O)NR$^7$R$^8$, S(=O)R$^6$, S(=O)$_2$R$^6$, P(=O)R$^6$R$^7$, P(=O)(OH)(OH), P(=O)(OH)(OR$^6$), P(=O)(OR$^6$)(OR$^7$), C≡N, NO$_2$, CH$_2$F, CHF$_2$, CF$_3$, Cl, Br, F, I and combinations thereof; or where p≥2 each R$^{11}$ and the carbon atoms to which they are attached may define a C$_5$-C$_{20}$ cycloaliphatic ring, a C$_2$-C$_{20}$ heterocycloaliphatic ring, a C$_5$-C$_{20}$ aryl ring, or a C$_3$-C$_{20}$ heteroaryl ring; and R$^6$, R$^7$ and R$^8$ are the same or different and are independently selected from the group consisting of C$_1$-C$_{20}$ aliphatic, C$_1$-C$_{20}$ heteroaliphatic, C$_3$-C$_{20}$ cycloaliphatic, C$_2$-C$_{20}$ heterocycloaliphatic, C$_5$-C$_{20}$ aryl, C$_3$-C$_{20}$ heteroaryl, and combinations thereof.

4. A method according to claim 3, wherein the enolisable C$_4$-C$_{50}$ cyclic organic anhydride is

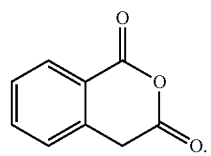 [SMILES: O=C1Cc2ccccc2C(=O)O1]

5. A method according to claim 1, wherein the bifunctional organocatalyst is selected from the group consisting of:

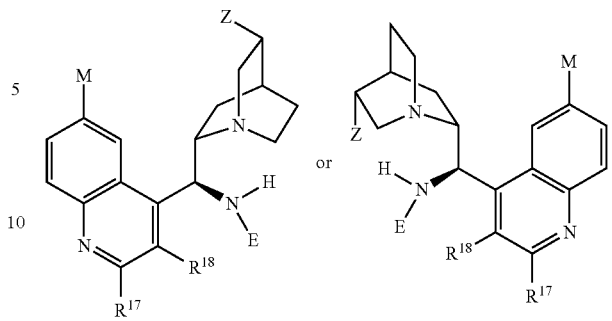

wherein

Z is C$_1$-C$_5$ aliphatic optionally substituted one or more times with at least one of a halogen, cyano, CF$_3$, NO$_2$, C$_1$-C$_5$ ketone, C$_1$-C$_5$ ester, C$_1$-C$_{10}$ amide, C$_1$-C$_5$ sulfone, C$_1$-C$_5$ sulfoxide and combinations thereof;

M is selected from the group consisting of H, OH, SH, O(C$_1$-C$_5$ aliphatic), and S(C$_1$-C$_5$ aliphatic);

R$^{17}$ and R$^{18}$ are the same or different and are independently selected from the group consisting of H, C$_3$-C$_{10}$ branched aliphatic, C$_3$-C$_{10}$ branched heteroaliphatic, C$_3$-C$_{20}$ cycloaliphatic, C$_2$-C$_{20}$ heterocycloaliphatic, C$_5$-C$_{20}$ aryl, C$_3$-C$_{20}$ heteroaryl, Br, I and combinations thereof; or R$^{17}$ and R$^{18}$ together with the carbon atoms to which they are attached define a monocyclic or polycyclic structure selected from the group consisting of C$_3$-C$_{20}$ cycloaliphatic, C$_2$-C$_{20}$ heterocycloaliphatic, C$_5$-C$_{20}$ aryl, C$_3$-C$_{20}$ heteroaryl; and E is a moiety selected from the group consisting of:

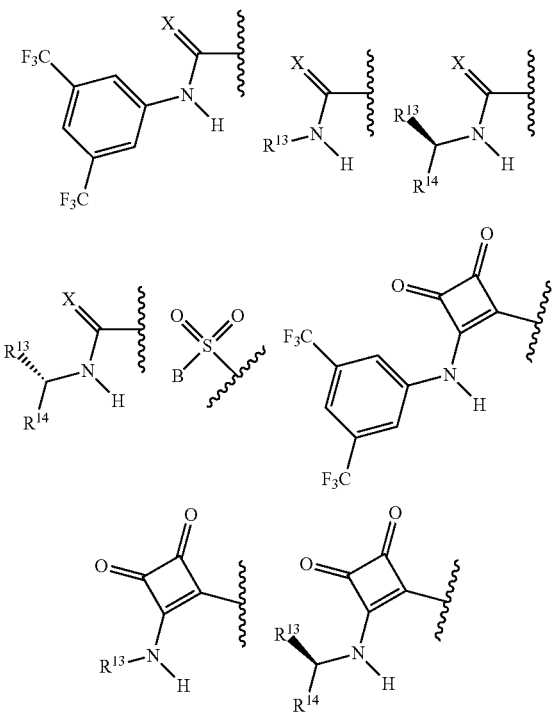

-continued

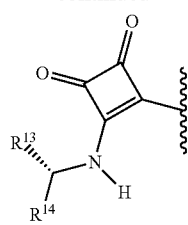

wherein X can be O or S;

B is selected from the group consisting of $C_1$-$C_{20}$ aliphatic, $C_1$-$C_{20}$ heteroaliphatic, $C_3$-$C_{20}$ cycloaliphatic, $C_2$-$C_{20}$ heterocycloaliphatic, $C_5$-$C_{20}$ aryl, $C_3$-$C_{20}$ heteroaryl, and combinations thereof optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof;

$R^{13}$ and $R^{14}$ are the same or different and are independently selected from the group consisting of $C_1$-$C_{20}$ aliphatic, $C_1$-$C_{20}$ heteroaliphatic, $C_3$-$C_{20}$ cycloaliphatic, $C_2$-$C_{20}$ heterocycloaliphatic, $C_5$-$C_{20}$ aryl, $C_3$-$C_{20}$ heteroaryl, and combinations thereof optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof; or $R^{13}$ and $R^{14}$ together with the carbon atom to which they are attached define a $C_3$-$C_{20}$ cycloaliphatic ring, $C_2$-$C_{20}$ heterocycloaliphatic ring, $C_5$-$C_{20}$ aryl ring, $C_3$-$C_{20}$ heteroaryl ring optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof.

6. The method of claim 1, wherein the bifunctional organocatalyst is

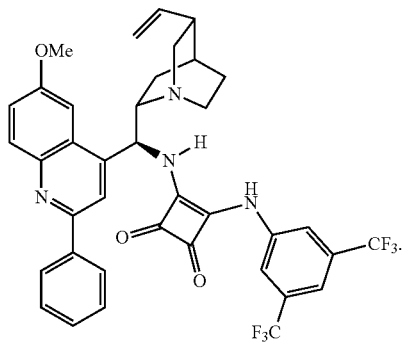

wherein

Z is $C_1$-$C_5$ aliphatic optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide and combinations thereof;

M is selected from the group consisting of H, OH, and O($C_1$-$C_5$ aliphatic);

$R^{17}$ is selected from the group consisting of $C_5$-$C_{20}$ aryl, and $C_3$-$C_{20}$ heteroaryl; and E is a moiety selected from the group consisting of:

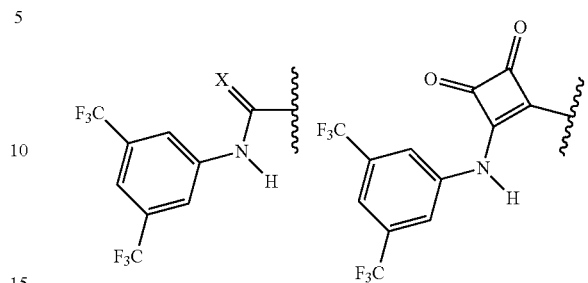

wherein X is O or S.

7. The method of claim 1, wherein the bifunctional organocatalyst is

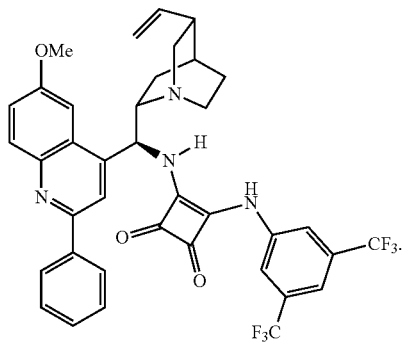 [SMILES: C=CC1CN2CCC1CC2[C@@H](Nc1c(Nc2cc(C(F)(F)F)cc(C(F)(F)F)c2)c(=O)c1=O)c1cc(-c2ccccc2)nc2ccc(OC)cc12]

8. The method of claim 1, wherein the bifunctional organocatalyst is selected from the group consisting of:

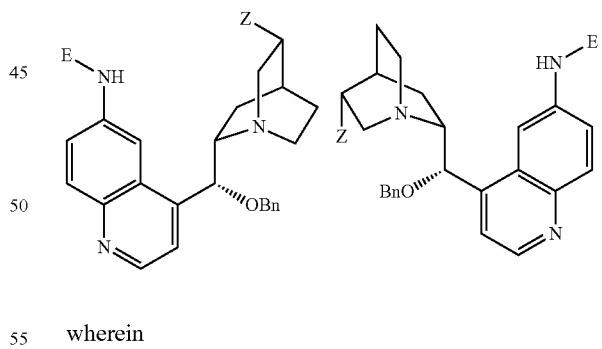

wherein

E is a moiety selected from the group consisting of:

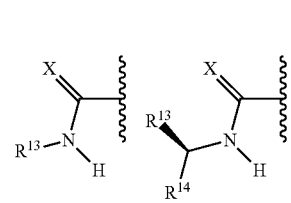

-continued

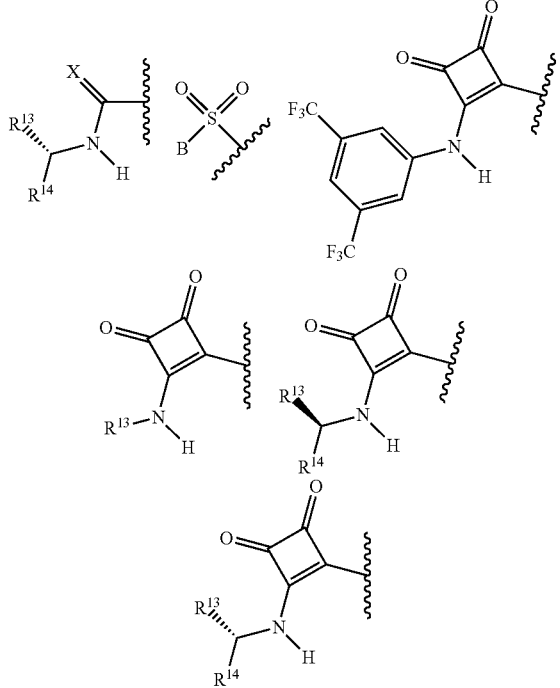

X is O or S;

B is selected from the group consisting of $C_1$-$C_{20}$ aliphatic, $C_1$-$C_{20}$ heteroaliphatic, $C_3$-$C_{20}$ cycloaliphatic, $C_2$-$C_{20}$ heterocycloaliphatic, $C_5$-$C_{20}$ aryl, $C_3$-$C_{20}$ heteroaryl, and combinations thereof optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof; and $R^{13}$ and $R^{14}$ are the same or different and are independently selected from the group consisting of $C_1$-$C_{20}$ aliphatic, $C_1$-$C_{20}$ heteroaliphatic, $C_3$-$C_{20}$ cycloaliphatic, $C_2$-$C_{20}$ heterocycloaliphatic, $C_5$-$C_{20}$ aryl, $C_3$-$C_{20}$ heteroaryl, and combinations thereof optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof; or $R^{13}$ and $R^{14}$ together with the carbon atom to which they are attached define a $C_3$-$C_{20}$ cycloaliphatic ring, $C_2$-$C_{20}$ heterocycloaliphatic ring, $C_5$-$C_{20}$ aryl ring, $C_3$-$C_{20}$ heteroaryl ring optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof.

* * * * *